United States Patent
Schacht et al.

(10) Patent No.: US 6,458,386 B1
(45) Date of Patent: Oct. 1, 2002

(54) MEDICAMENTS BASED ON POLYMERS COMPOSED OF METHACRYLAMIDE-MODIFIED GELATIN

(75) Inventors: Etienne Schacht, Staden (BE); An Van Den Bulcke, Ghent (BE); Bernard Delaey, Zingem (BE); Jean-Pierre Draye, Chaste (BE)

(73) Assignee: Innogenetics N.V., Ghent (BE)

( * ) Notice: Subject to any disclaimer, the term of this patent is extended or adjusted under 35 U.S.C. 154(b) by 0 days.

(21) Appl. No.: 09/424,432

(22) PCT Filed: Jun. 3, 1998

(86) PCT No.: PCT/EP98/03320

§ 371 (c)(1),
(2), (4) Date: Jan. 28, 2000

(87) PCT Pub. No.: WO98/55161

PCT Pub. Date: Dec. 10, 1998

(30) Foreign Application Priority Data

Jun. 3, 1997 (EP) .............................. 97870083

(51) Int. Cl.$^7$ ................................. A61K 9/14
(52) U.S. Cl. ................ 424/488; 424/443; 424/444; 424/445; 424/447; 424/448; 424/426; 424/428; 424/484
(58) Field of Search ................ 424/443, 444, 424/445, 447, 448, 426, 428, 484, 488

(56) References Cited

U.S. PATENT DOCUMENTS

| 4,768,523 A | * 9/1988 | Cahalan et al. ............. 128/785 |
|---|---|---|
| 5,147,344 A | 9/1992 | Sachau et al. ............. 604/368 |
| 5,792,090 A | * 8/1998 | Ladin ............. 602/48 |

FOREIGN PATENT DOCUMENTS

| DE | 31 46 841 A | | 6/1983 | .......... A61K/37/12 |
|---|---|---|---|---|
| EP | 174 849 | * | 3/1986 | |
| EP | 0 308 330 A | | 3/1989 | .......... C12N/11/10 |
| EP | 0 446 473 A | | 9/1991 | .......... A61L/25/00 |
| EP | 0 702 959 A | | 3/1996 | .......... A61K/37/24 |
| JP | 05 262800 A | | 10/1993 | .......... C07K/17/08 |
| WO | WO 95 34328 A | | 12/1995 | .......... A61L/15/16 |

* cited by examiner

Primary Examiner—Thurman K. Page
Assistant Examiner—Lakshmi Channavajjala
(74) Attorney, Agent, or Firm—Howrey Simon Arnold & White, LLP

(57) ABSTRACT

The present invention relates to a composition comprising a biopolymer matrix comprising cross-linked vinyl-derivatives of gelatin, or co-polymerized methacrylamide modified gelatin with vinyl-modified polysaccharides, or cross-linked vinyl-substituted polysaccharide and gelatin being physically entrapped in a semi-interpenetrating network. Preferably said polysaccharide comprises dextran or xanthan. The present invention also relates to a wound dressing or a controlled release device comprising said biopolymer matrix. Preferably said matrix is in the form of a hydrated film, a hydrated or dry foam, dry fibers which may be fabricated into a woven or non-woven tissue, hydrated or dry microbeads, dry powder, or covered with a semipermeable film so as to control the humidity of the wound covered with the dressing, with the permeability chosen so as to maintain this humidity within a therapeutically optimal window.

21 Claims, 14 Drawing Sheets

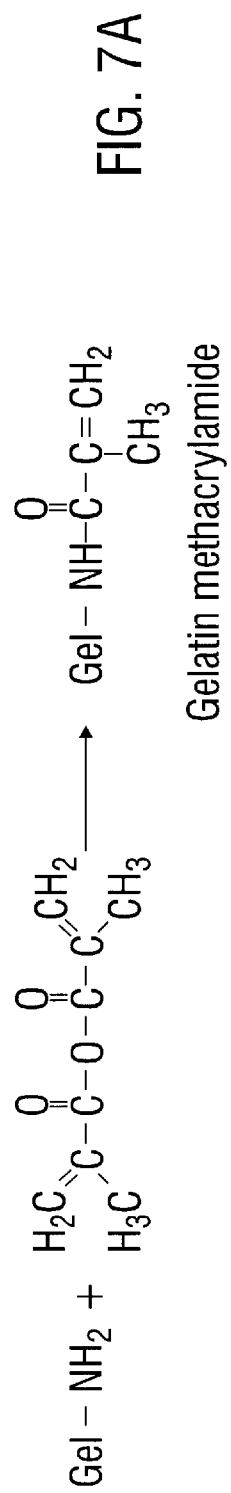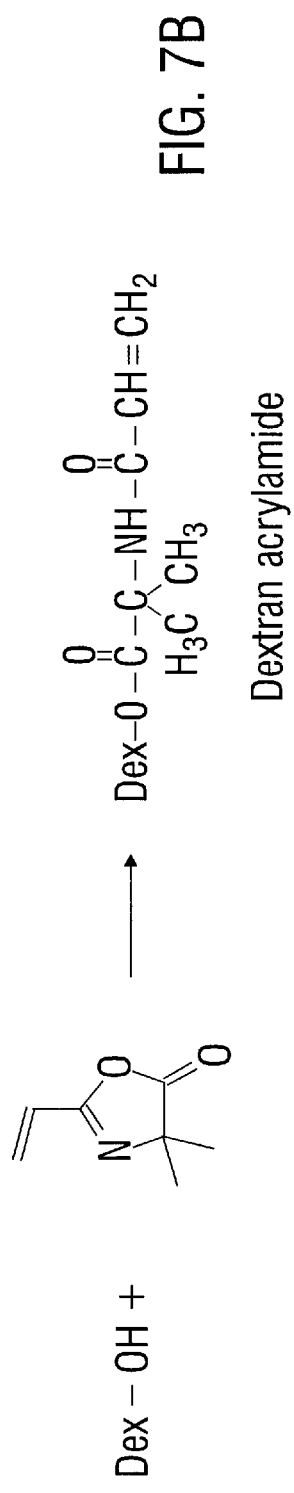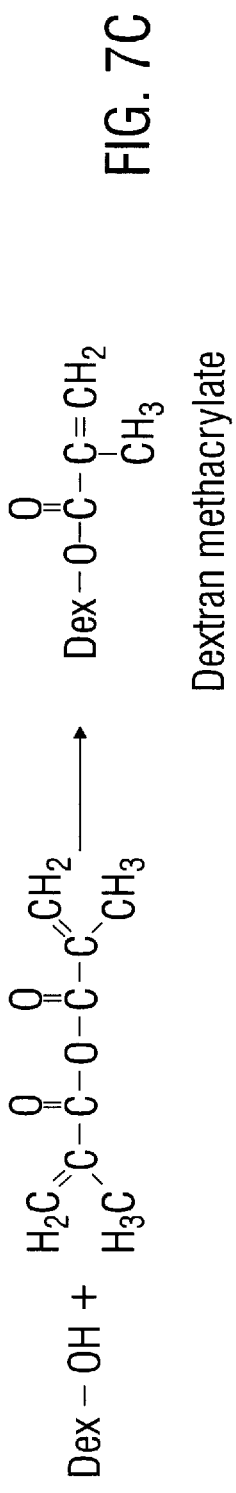

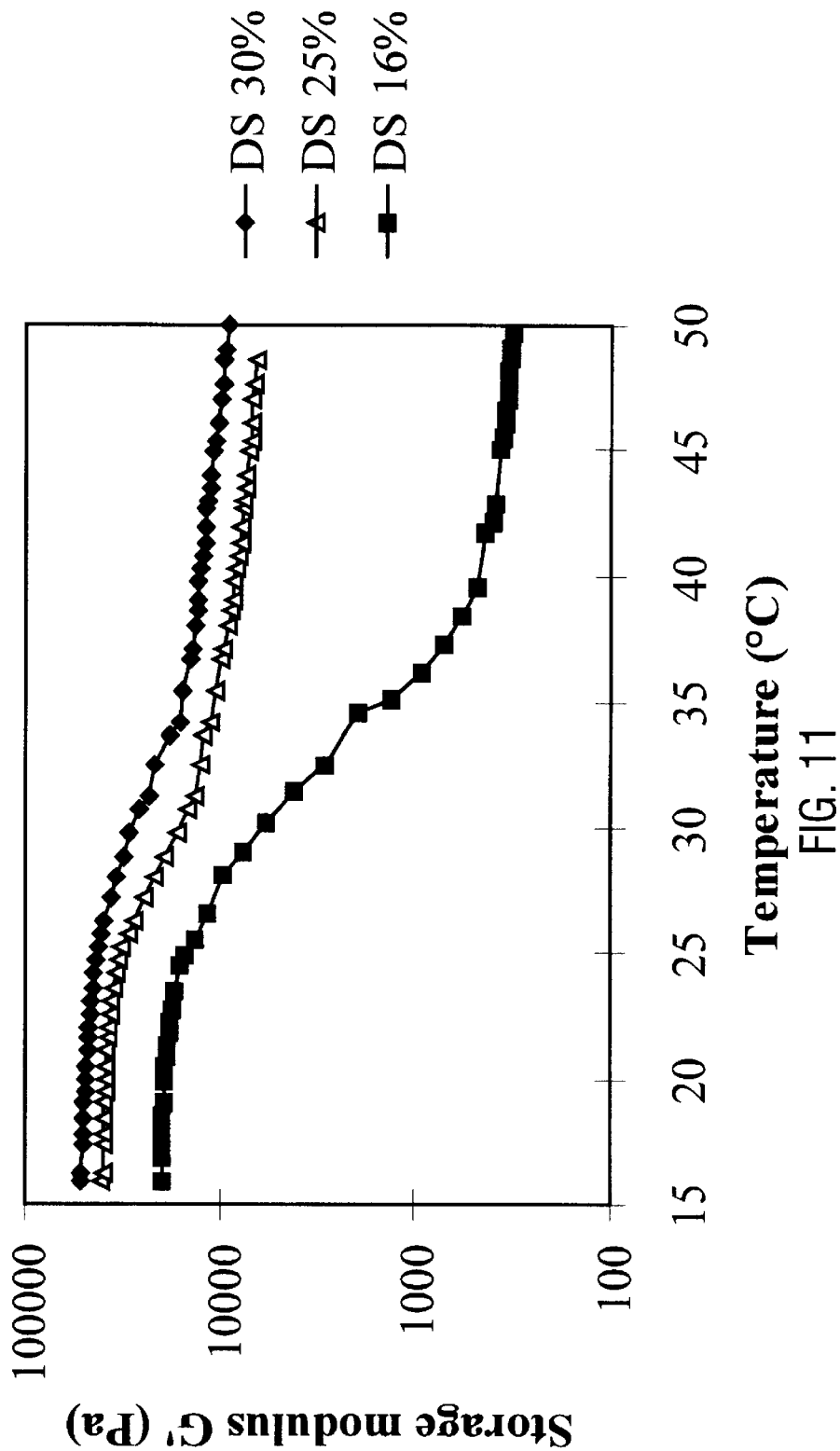
FIG. 11 EFFECT OF 6 KGY DOSIS ON GELATIN METHACRYLAMIDE GELS WITH DIFFERENT DEGREE OF SUBSTITUTION

MEDICAMENTS BASED ON POLYMERS COMPOSED OF METHACRYLAMIDE-MODIFIED GELATIN

This application is a 371 of PCT/EP98/03320, filed Jun. 3, 1998.

FIELD OF THE INVENTION

The present invention relates to wound dressing materials comprising either cross-linked methacrylamide modified gelatin, or co-polymerized methacrylamide modified gelatin with vinyl-substituted polysaccharides, or cross-linked vinyl-substituted polysaccharides and gelatin being physically entrapped in a semi-interpenetrating network. The material is useful for the covering of a variety of wound types, particularly chronic wounds and burns. The material is also suitable for the controlled release of drugs. When loaded with suitable growth factors or wound repair promoting substances, the matrix is useful for the fabrication of wound dressings for the treatment of a variety of wound and burns.

BACKGROUND OF THE INVENTION

A very large number of people are suffering from chronic non-healing skin wounds. A common feature in the treatment of these wounds is that they need covering for optimal healing. The beneficial effect of covering wounds is situated at different levels and is dependent on the type of dressing material used. For acute wounds, suitable dressings may help to achieve haemostasis and thus control blood loss. Also, covering of wounds effectively shields the wound from the environment, thus protecting it from microbial contamination. Furthermore, some so-called occlusive or semi-occlusive wound dressings have the capability of maintaining the wound moist, which is beneficial for healing. Finally, some wound dressings may themselves directly promote the healing process, for instance because they contain components which directly promote cell growth or migration or which attract or activate cells from the immune system which themselves secrete growth-promoting substances. Other dressings may contain antimicrobial substances, which are helpful to control infection of the wound.

Over time, a surprisingly wide variety of dressing materials have been used for wound covering, many of which are currently commercially available. Each of them has its own indications, dependent on wound type, depth, size, absence or presence of infection, level of exudate formation, etc.

Cotton gauze, for instance, is widely used as wound dressing. It has the advantage of being cheap, but the disadvantage of being not occlusive and sometimes becoming encrusted into the wound. To prevent this, these dressings are sometimes impregnated with a greasy substance, such as paraffin. A commercially available example of such a dressing is Jelonet™ (Smith and Nephew, UK).

Another class of wound dressings are the absorptive hydrogel dressings. These have a high capacity for the absorption of wound exudate. They consist of hydrophilic polymers such as gelatin, polysaccharides, polyacrylamide, etc, which swell upon contact with wound fluid and can absorb several times their own weight of exudate. Commercially available hydrogel dressings include Intrasite gel (Smith and Nephew, UK) and Vigilon (CR Bard, USA). A special type of hydrogels are the alginates, which are hydrophilic polysaccharides extracted from seaweed. They are produced as thin non-woven tissues or as ropes. Upon contact with the wound fluid, they turn into a gel which has a high absorptive capacity for wound fluid. Examples include Kaltostat (Brit-Cair, UK) and Sorbsan (Steriseal, UK).

Another type of dressings are the occlusive or semi-occlusive dressings. In their simplest form, they usually exist of a thin, flexible plastic membrane, e.g. from polyurethane. To facilitate application, these dressings are usually fabricated with a self-adhesive coating. These dressings are called occlusive because they limit water evaporation from the wound surface, thus keeping it moist. Examples of such dressings are Opsite (Smith and Nephew, UK) and Tegaderm (3M, USA). Examples of semi-occlusive dressings are Omiderm (Iatro Medical Systems, UK) and Exkin (Koninklijke Utermöhlen, The Netherlands). The latter dressings allow a slightly higher evaporation rate, resulting in a semi-dry wound surface.

A more complex type of occlusive dressings are the hydrocolloid (HCD) dressings. These are made up of hydrocolloid particles (e.g. consisting of gelatin, pectin, carboxymethyl cellulose, etc) embedded in a hydrophobic matrix (e.g. a polyisobutylene, styrene-isoprene-styrene copolymer). These dressings may be backed with an occlusive membrane and/or a foam plastic layer. In addition to being occlusive, HCD dressings have a high absorptive capacity, making them very suitable for the treatment of wounds producing high amounts of exudate. These beneficial properties have made HCD dressings among the most successfully used dressings for the treatment of chronic ulcerations of the skin. Commercially available examples of these dressings include DuoDERM© (Convatec, UK), Tegasorb™ (3M, USA), and Comfeel Coloplast, Denmark)

Although highly successfull recent reports suggest that HCD dressings may nevertheless induce undesirable side reactions in the treated tissues. For example, Van Luyn reports that DuoDERM (Convatec, UK), Biofilm (Biotrol SPA, France), Comfeel (Coloplast, Denmark) and Ulcer dressing (Johnson and Johnson, USA), all of which are HCD dressings, fall within the high toxicity class when tested in a methylcellulose assays using human skin fibroblasts as target cells (Van Luyn, M. Doctoral Thesis, 1992, State University Groningen, The Netherlands; Van Luyn, M., Abstract Book of the joint WHS/ETRS meeting, Amsterdam, 1993 p114). All the HCD dressings tested by this author highly inhibited cell growth (>70%) and induced strongly deviant morphologies in the surviving cells. Leek et al. (Abstract Book of the Second Annual WHS Meeting, Richmond, Va., USA, p75, 1992) have tested four HCD dressings in full-thickness excisional wounds in pigs. All dressings induced development of granulomatous lesions between 4 and 10 days post wounding and exhibiting little evidence of resolution at 3 months post wounding. The most severe reaction was obtained with DuoDERM and Intrasite HCD. Rosdy and Clauss (J. Biomedical Mat. Res. 24, 363–3777, 1990) found that the HCD dressing Granuflex™ (Bristol-Myers Squibb, USA) induced cytopathic effects on MRC5 fibroblasts and epidermal cells upon direct contact. Young et al. (J. Invest. Dermatol. 97, 586–592, 1991) describe in an animal model system the development of deep-seated foreign body type reactions and granulomata in healed wounds which were treated with HCD dressings. Our own experiments with the HCD dressing DuoDERM™ show that this dressing results in a marked and chronic inflammatory response when placed in full thickness wounds in pigs.

The above mentioned data suggest that, while HCD dressings may promote wound healing in the short term, their use is often associated with undesirable inflammatory effects. Therefore, it is clear that there is a need for a wound dressing displaying the beneficial properties of HCD dressings, yet resuking in substantially less chronic inflammation or foreign body response. Such a wound dressing would stimulate granulation tissue formation, be absorptive and eventually be biodegradable within a limited time frame.

Gelatin, which is a denatured form of the protein collagen, has been used in a variety of wound dressings and controlled release systems. Because of their relative low melting point, gelatin gels are not very stable at body temperature. Consequently, it is necessary to stabilize these gelatin gels before they can be used for wound healing purposes. This is usually done by establishing cross-links between the protein chains by treating gelatin with either formaldehyde or glutaraldehyde. Alternatively, this can be accomplished by cross-liming of gelatin with polyaldehydes produced by partial oxidation of polysaccharides such as dextran (Schacht E H, Nobels M, Vanteenkiste S, Demeester J, Fransen J, Lemahieu A. Polym Gels Networks 1993; 1: 213–224). Cross-linked gelatin may be fabricated into dry sponges which are useful for inducing haemostasis in bleeding wounds. Commercially available examples of such sponges include Spongostan® (Ferrosan, Denmark) and Gelfoam (Upjohn, USA). A major disadvantage of these sponges is that the cross-linking agent used (formaldehyde or glutaraldehyde) is toxic for cells. The negative effect of glutaraldehyde cross-linking is exemplified, for instance, by the findings of de Vries et al (Abstract Book of the Second Annual Meeting of the WHS, Richmond, USA, p51, 1992). These authors showed that glutaraldehyde cross-linked collagen lattices were toxic for cells, whereas the non cross-linked variety was not. Therefore, despite their beneficial haemostatic properties, these products are not very optimal as wound dressings for the treatment of problematic wounds such as chronic ulcers or burns. Consequently, a gelatin-based wound dressing which uses a different, less toxic, cross-linking technology would be very desirable. Dextran is a polysaccharide which is also widely used for medical purposes, and which may also be used in a wound dressing. For example, PCT patent application No. WO 94/27647 (Smith and Chakravarty, published Aug. 12, 1994) teaches the fabrication of a polymer composition comprised of cross-linked dextran, where the cross-linking groups consist of linear imidocarbonate or carbonate groups. This polymer can be incorporated in a wound dressing. An important feature of this polymer composition is that it is hydrolytically labile. This means that hydrated forms of the material are inherently unstable, and that the polymer can only be stored for prolonged periods when dehydrated.

Schacht et al., in a European patent published under No. 0308330, disclose a polymer composition comprising gelatin, cross-linked with oxidized polysaccharides wherein proteins, enzymes or micro-organisms can additionally be immobilized.

Apart from the development of improved dressings, increasing attention has been given over the last years to the possible use of growth factors to promote the healing of wounds, in particular burns and ulcers. Following are but a few of the scientific reports describing the use of growth factors for promoting wound healing in humans. Epidermal Growth Factor (EGF) has been used for the treatment of skin graft donor sites (Brown et al, N. Engl. J. Med. 321, p76–79, 1989) and chronic ulcers (Brown et al., Plast. Reconstr. Surg. 88, p. 189–194, 1991). This same factor has also successfully been used in ophthalmology for the topical treatment of traumatic corneal ulcers (Scardovi et al., Ophthalmologica 206, p.119–124, 1993) and to promote endothelial wound healing in human corneas (Hoppenreijs et al., Invest. Ophthalmol. Vis. Sci. 33, p1946–1957, 1992). EGF eye drops are commercially available under the trade name Gentel® from Inpharzam S. A. (Cadempino, Switzerland). Basic Fibroblast Growth Factor (bFGF) has been used for the treatment of chronic pressure sores (Robson et al, Ann. Surg. 216, p.401–408, 1992) and for the treatment of experimentally induced suction blisters in humans (Lyonnet et al., J; Invest. Dermatol 96, p.1022, 1991). Transforming Growth Factor-$\beta$ (TGF$\beta$) was found to have beneficial effects in the treatment of full thickness macular holes in human eyes (Glaser et al., Opthalmology 99, p1162–1173). Platelet Derived Growth Factor (PDGF) was found to be a wound healing stimulator of chronic pressure ulcers in humans (Robson et al., Lancet 339, p.23–25, 1992). Human Growth Hormone has been reported to accelerate wound healing in children wth large cutaneous burns (Gilpin et al., Ann. Surg. 220, p. 19–24, 1994). Platelet lysate, which is a crude preparation containing a mixture of several growth factors, has also been found to stimulate the healing of chronic ulcers (Knighton et al., Surgery Gyn. Obst. 170, 56–60, 1990). The latter preparation has been commercialized under the trade name Procuren by Curative Technologies, Inc (USA). Our own studies with crude keratinocyte lysates, which also contain several cell growth promoting activities, have shown to increase the healing speed of burns wounds and to enhance epithelialisation of middle ear defects in chronic otorrhea patients and after tympanoplasty.

One common problem with all aforementioned studies is to find an efficient way for the controlled delivery of the active substances to the wound. In most cases, these substances are simply applied as an aqueous solution, or at best as a formulation in a semi-liquid gel or cream Using such formulations, most of the active substance is released in the wound site very rapidly. Nevertheless, it is known that many growth factors are relatively unstable and it is expected that their half life in the wound environment is relatively short. This means that there is a need for a device which would allow the controlled release of the active substance over a prolonged period, whilst protecting the still unreleased factor from premature degradation. This would significantly lower the cost and increase the efficiency of growth factor wound therapy by reducing the necessary dose and the number of applications. Several strategies and materials have been considered for the controlled release of peptide growth factors and similar substances. Following are a few of the approaches which have been reported in the scientific literature or for which patent applications have been filed.

One class of controlled release devices consists of synthetic biodegradable polymers. For instance, poly-lactide-glycolides (PLG) are hydrolytically degradable polymers which can be used for the slow release of variable pharmaceutical substances including bioactive macromolecules such as calcitonin, LHRH, somatostatin, insulin, interferon and vaccines (Lewis, Pharmaceutical manufacturing International, 1993, p99–105). Due to the use of organic solvents, incorporation of biologically active peptides or proteins into PLG often results in their inactivation. Although this can be circumvented by the production of physical PLG/peptide mixtures (e.g. by compression molding of powder mixes), these may be less suitable as wound dressings because of their rigidity and brittleness.

Apart from synthetic polymers, a wide variety of naturally occurring polymers, or modifications thereof, have been used for controlled release of bioactive peptide factors. An example of this is methylpyrrolidinone chitosan fleeces loaded with bFGF (Berscht et al., Biomaterials 15, 593–600, 1994). A particular controlled release composition is disclosed in WO 92/09301 by Greisler, which teaches the use of growth factor-containing fibrin tissue sealant for acceleration of wound healing. Products according to the latter invention would probably be relatively expensive, due to the high cost of commercially available fibrin glues adhesives.

A frequently used biopolymer for controlled release is also gelatin. Collagen-containing gelatin sponges for protein drug delivery have been disclosed in patent applications EP 0568334 (published Mar. 11, 1994) and WO 93/21908. Golumbek et al., in Cancer Res. 53, p5841–5844(1993), describe the use of gelatin microspheres loaded with IFNγ or GM-CSF as potential cancer therapy vaccines Cortesi et al. (Int. J. Pharm. 105 p.181–186, 1994) describe the use of gelatin microspheres for the release of synthetic oligonucleotides and PCR-generated DNA fragments. The synthesis of gelatin microspheres containing Interferon was reported by Tabata and Ikada (Pharm. Res. 6, p.422–27, 1989). Shinde and Erhan (Bio-Med. Mat. Eng. 2, p.127–131, 1992) describe flexibilized gelatin films for the release of insulin.

As discussed above, the commonly used glutaraldehyde or formaldehyde for cross-linking these gelatin-based biomaterial have the disadvantage of being toxic for the cells. In addition to their toxic properties, glutaraldehyde and formaldehyde are also expected to affect the biological activity of incorporated bioactive protein substances when cross-linking is carried out after addition of these substances to the system Consequently, a gelatin-based slow release device which uses a different, less toxic, cross-linking technology would be very desirable for the fabrication of for instance, growth factor-medicated dressings.

SUMMARY OF THE INVENTION

The present invention thus aims at providing a suitable wound dressing.

The present invention also aims at providing a suitable slow or controlled release device.

The present invention further aims at methods for producing and using said wound dressings or said controlled or slow release devices.

The present invention relates to the discovery that hydrogels prepared with chemically modified and cross-linked gelatin constitute excellent medicaments, more particularly dressings for the treatment of wounds and the release of bioactive agents. The gelatin according to the present invention is modified with methacrylamide side groups which can be radically cross-linked. This concept allows to include polysaccharides and other water soluble polymers carrying radically polymerisable side groups e.g. acrylamide or methacrylate-side groups. Hydrogels can be prepared by physically entrapping gelatin during the cross-linking of the methacrylinde modified polysaccharides to form a semi-interpenetrating network (SIPN) or by the cross-linking of polysaccharides and gelatin both methacrylamide modified. The feasibility of preparing such hydrogels was demonstrated by using either an acrylamide or a methacrylate derivative of dextran, a polysaccharide particularly suited for use in the present invention. In Example 1, the preparations of vinyl-modified gelatin, acrylamide-modified dextran, dextran methacrylate and the preparation of the hydrogel films are exemplified.

One of the advantages of the presently disclosed medicament are that it comprises a biodegradable material. Nevertheless, since biodegradability is not obtained through the use of hydrolytically cleavable bonds, the object of our invention is sufficiently stable in a hydrated form to allow prolonged storage. Unlke non cross-linked gelatin it also has a melting point sufficiently high to remain on the wound site in an intact form for a sufficiently long time. An advantage is that one of the embodiments of the disclosed dressing offers the possibility to immobilize sulfated dextrans or similar poly-anionic molecules into the dressing, a modification which enhances the binding of added wound repair modulating factors or of in situ produced heparin-binding factors.

According to a second aspect, the present invention relates to the finding that the above-mentioned cross-linked gelatin constitutes an ideal biopolymer matrix for the incorporation and subsequent controlled release of bioactive peptide factors. Therefore, pharmaceutically active peptides or polypeptides can be incorporated in the matrix by mixing them with the solubilized gelatin component followed by radical cross-linking of the vinyl side groups to obtain a stabilized cross-linked gel containing the polypeptides in a releasable form. Polypeptide incorporation during the hydrogel production process is more rapid and more efficient than the alternative procedure of incorporating the polypeptides by sorption process (eg by soaking the dehydrated or partially dehydrated matrix in a solution containing the polypeptides). Such medicated cross-linked gelatin matrix may be used for several therapeutical applications, in particular for the fabrication of medicated wound dressings.

The term "biopolymer matrix" according to the present invention refers to a matrix composed of modified gelatin, or modified gelatin and modified polysaccharides, or gelatin and modified polysaccharides, as defined above having as a basic property that biodegradable, In a preferred embodiment, the proposed wound dressing consists of a hydrated sheet or film of matrix as defined above, backed with an occlusive or semi-occlusive film Occlusive in this context means that the film has a permeability for water which is sufficiently low to prevent desiccation of the wound, yet sufficiently high to prevent excessive accumulation of exudate below the wound dressing.

In another embodiment, the wound dressing is fabricated in the form of dehydrated or dry microparticles. These microparticles are especially suited to be applied into deep, highly exudative wounds. By virtue of the high fluid-absorptive capacity of the particles, the wounds may in this way be cleaned from excess exudate and slough.

In yet another form, the proposed polymer is fabricated into a flexible dehydrated foam. Such a foam may be easily applied onto shallow wounds and also has a high absorptive capacity. But any other format which respects the polymer properties of stability, biodegradability and retention of bioactive growth factors is also conceivable. In this respect, a hydrated foam may have other quantities.

The proposed polymer can also be used for the fabrication of a wound dressing containing one or more wound repair-promoting substances. Examples of such substances are for instance growth factors such as EGF, TGF-α, FGFs, PDGFs, amphiregulin, HB-EGF, betacellulin, TGF-β, IGFs or other mitogens or their antagonists which may modulate the wound repair process. Such a medicated wound dressing can be produced in different forms, including flexible sheets, foams, microparticles, fibres to create woven or non-woven tissues, etc. One of the embodiments of the invention concerns the production of a wound dressing containing multiple layers, where each layer contains a different active component, so as to achieve a programmed delivery of the different components over time. In another embodiment, suitable affinity groups are finked to the polymer matrix, to increase the affinity of the matrix for the incorporated active substances, thus decreasing their release rate and/or to protect them from premature degradation or inactivation. Examples of such affinity groups include polysulfated oligo- or polysaccharides such as heparin, heparan sulfate, chondroitin sulfate, dermatan sulfate, dextran suffite, or functional analogs or fragments thereof which have an affinity for heparin binding growth factors such as the FGFs, amphiregulin and HB-EGF. Any proteoglycan containing glycosaminoglycan chains capable of binding to heparin-binding factors is thereby also included. Possible affinity groups also include monoclonal or polyclonal antibodies or microproteins as obtained through phage display, and which have a high and selective affinity for specific growth factors.

DETAILED DESCRIPTION OF THE PREFERRED EMBODIMENTS

The present invention relates to the discovery that hydrogels composed of gelatin or gelatin and polysaccharides, as defined above, constitute an excellent material for the preparation of dressings suitable for the covering and treatment of wounds. In addition, the material also displays unexpectedly favourable controlled release properties for the delivery of therapeutic substances, particularly to wounds. The hydrogels are prepared by the cross-linking of solubilized gelatin or gelatin derivatives. Gelatin is a denatured form of the connective tissue protein collagen. Several types of gelatin exist, depending on the source of collagen used, and on the extraction and production process employed One type of gelatin is extracted from animal bones, while another type is extracted from animal skin. Usually, the animal material is from bovine or porcine origin. Depending on the extraction process, two types of gelatin can be prepared: the A (or acidic) type, which is prepared by acid hydrolysis of the collagen and which has an isoelectric point of about 8, and the B (or basic) type, which is prepared by basic hydrolysis of the collagen and which has an isoelectric point of about 5. Both types of gelatin are usable for preparation of hydrogel matrices, as defined above, suitable for the present invention. An important property of gelatin is that it forms gels with a certain rigidity. The rigidity of these gels is expressed by the Bloom number of the gelatin. For the purpose of this invention, gelatins with a variety of Bloom numbers are usable. However, Bloom numbers of at least 150, preferably at least 200, more preferably at least 250 are preferred, because they offer hydrogels matrices of a high mechanical strength which can easily be fabricated in films or sheets.

In the present invention acrylamide or methacrylate modified dextran was selected as examples of a vinyl substituted polysaccharide that can be co-polymerized with vinyl-substituted gelatin. However, it shall be obvious to the person skilled in the art that other polysaccharides and vinylsubstituted water soluble polymer with suitable viscosity, molecular mass and vinyl content properties can also be used. An example of such another polysaccharide is xanthan. Although different polysaccharides are thus conceivable for the purpose of this invention, we shall from hereon only refer to the use of acrylamide substituted dextrans. This is simply for the sake of clarity and should in no way be considered as a limitation with respect to the range of possible polysaccharides usable within the framework of the invention. The molecular weight of the dextran used for the fabrication of wound dressings according to the invention is preferably below 5,000,000, more preferably between 10.000 and 100,000, in such a way that the viscosity of the aqueous solution of the dextran is not too high, for example between 0.1 and 1 Pa.s for a 2% solution (as measured using a Brookfield LVT viscosimeter operated at 30 cycles).

Substitution of dextran with acrylamide or methacrylate side groups was carried out according methods described in the literature. For instance such derivatives can be obtained by reaction of the polysaccharide with 2-vinyl-4,4,-dimethyl-2-oxalin-5-one (vinyldimethylazolacton). Cross-linking of gelatin methacrylamide or co-polymerization of gelatin methacrylamide with vinyl-substituted polysaccharide, or cross-linking of vinyl-substituted polysaccharides to entrap gelatin in a semi-interpenetrating network, are performed in aqueous medium in the presence of a radical initiator such as ammonium persulfate+N, N'tetramethylethylene diamine. Cross-linking can also be achieved by light-induced radical formation. Example 1 shows examples for the preparation of vinyl-modified gelatin and dextran, and for the preparation of hydrogel films by radical cross-linking after exposition of the vinyl-derivatives to UV-light in the presence of a photoinitiator. Example 2 shows the visco-elastic properties a gelatin hydrogel films prepared by radical cross-linking of methacrylamide-modified gelatin.

Although the procedure described above is preferred, it will be clear to the person skilled in the art that other methods leading to the introduction of vinyl side groups are also possible, for instance, by treatment with methacrylic anhydride in an organic solvent such as dimethylsulfoxide. Thereafter, the modified dextran can be conveniently purified and separated from low molecular weight reaction components by classical purification methods. Examples to accomplish this include, but are not limited to: precipitation (for instance by addition of acetone, methanol or isopropanol) or dialysis, ultrafiltration or gel permeation chromatography, followed by lyophilisation.

The speed and the degree of cross-linking are dependent on a variety of parameters, such as the concentration, the type of gelatin and its degree of vinyl substitution, the molecular weight and degree of vinyl substitution of the polysaccharides, etc.

According to the present invention, the gelatin hydrogels prepared as described above can be used for the fabrication of a variety of wound dressings.

According to a preferred embodiment, gelatin hydrogels are fabricated into a thin sheet or film, suitable for application onto a wound surface. There exist several known technologies to accomplish this. For instance, a solution of vinyl-substituted gelatin (kept at a temperature higher then the gelification point of the gelatin used, usually >30° C.) can be mixed with a solution of the initiator and be poured into a suitable cast before any appreciable cross-linking takes place. Afer the cross-linking process is finished, the film can be removed from the cast. Another way to form films is to use one of the processes utilized in the photographic industry for the preparation of photographic films and papers. For the purpose of this invention, the thickness of the films shall preferably range between 0.1 and 2 mm, more preferably between 0.3 and 1 mm, although differently sized films may be appropriate for some applications.

When a film according to the procedure described above is placed onto a wound for a prolonged period, it is possible that dehydration still takes place because fluid can evaporate from the surface of the film. To prevent this, the gelatin hydrogel wound dressing film can be additionally covered by one of the commercially available occlusive or semi-occlusive wound dressing films, for example a polyurethane such as Opsite or Tegaderm However, a better solution is provided according to another preferred embodiment of the present invention where a gelatin hydrogel film is directly laminated onto a suitable occlusive membrane during the production process. For instance, particularly well suited plastic films are those from the Pebax series, such as Pebax 1205, which are produced by Elf. This type of film has a very low water vapour permeability, making it very suitable for the fabrication of wound dressings intended for use on relatively dry wounds. For application on more exudative wounds a higher evaporation rate is desirable, to prevent excessive accumulation of fluid under the dressing. In this instance, a backing membrane with higher water vapour permeability may be preferred, such as those manufactured by Utermöhlen in The Netherlands (Exkin) or by Iatro Medical Systems in the UK (Omiderm). To the person skilled in the art it shall be obvious that, depending on the type of wound, the degree of exudate formation and the desired frequency of dressing change, other backing films with different water vapour permeability properties can be used, to obtain an optimal fluid balance at the wound surface.

According to another embodiment, gelatin hydrogels are fabricated into a hydrated or dehydrated particulate wound dressing. Several techniques are known to achieve this. A dry gelatin hydrogel powder or granulate may be produced by dehydration of a solid gelatin hydrogel mass after cross-linking, followed by powdering the dehydrated material. Dehydration may be obtained for instance by drying in a stream of dry air, lyophilisation, organic solvent extraction, etc. After the powdering or granulation step, particles of a desired size may be selected, for instance by sieving through a series of sieves with a suitable mesh size. For the manufacturing of spherical or substantially spherical gelatin hydrogel particles or microbeads, one can generate a spray by pushing a freshly prepared solution of vinyl-substituted gelatin (or a mixture of vinyl-substituted gelatin and vinyl-substituted polysaccharides or a mixture of vinyl-substituted polysaccharides and gelatin), through an appropriate atomization nozzle. It has to be understood that the sizes of the spray drops will vary according to the type of application and can be determined by choosing the appropriate nozzle type, pressure and capacity for the atomization process. Another possibility is to emulsify the freshly prepared solutions described above with a non-water miscible solvent such as an aliphatic or aromatic hydrocarbon or an oil. To create spherical particles of a larger size, the solutions may alternatively be added dropwise to the non-water miscible solvent. Other techniques to produce hydrated or dehydrated gel particles, known to the person skilled in the art, may also be used to prepare a particulate wound dressing according to this invention. Such a particulate wound dressing may be useful for the treatment of a variety of wound types, but especially for the treatment of relatively deep and highly exudative wounds, such as some chronic ulcers or decubitus wounds. When applied in a dehydrated form they have the property of absorbing exudate. This is a highly desirable feature, since removal of excess exudate and slough is an important therapeutical goal with respect to the prevention of microbial colonization, to the limitation of further necrotization and to the relieve of discomfort for the patient. Such a particulate wound dressing can also be used in its hydrated form (i.e. by omitting the dehydration process after particle preparation or by rehydrating dehydrated particles before application onto the wound). In this latter form, it can be applied for instance as a paste to wounds which produce less exudate. It shall be obvious that, depending on the needs of a particular wound type, the possibility also exists to use the particulate wound dressing in a partially hydrated form In the latter form, the dressing still would have substantial fluid absorptive properties, yet, by virtue of a certain stickiness, it would easily be applicable as a paste or be fabricated into a thin film. By adapting the type of gel, wound dressings can be designed that are appropriate for treatment of other wounds such as corneal wounds or defects, tympanic membrane reconstructions, or other middle ear reconstructions, or chronic otorrhea. It shall also be clear that the dehydrated, partially hydrated and fully hydrated forms of these particulate wound dressings can be suspended in any suitable aqueous or organic excipient to facilitate application. Examples of such excipients include, but are not limited to: paraffin oil, Vaseline, glycerol etc.

Another physical form into which the gelatin hydrogels wound dressings can be fabricated is a hydrated or dry foam. This can be achieved for instance by adding a suitable biocompatible detergent to the freshly prepared solutions of vinyl-substituted gelatin (or a mixture of vinyl-substituted gelatin and vinyl-substituted polysaccharides or a mixture of vinyl-substituted polysaccharides and gelatin), to which is added a suitable radical initiator, followed by introducing small gas bubbles into the solution. The gas can be air, nitrogen, helium or another gas, preferably a gas which is not water soluble, non-toxic and chemically inert. Other techniques known in the art for producing foams are also suitable, provided they do not result in the introduction of non-biocompatible components or do not interfere with the cross-linking process. Foams can be used either in the hydrated form, or be also partially or completely dehydrated. They can be produced as sheets, rods, plugs, pads, etc., or in any other form which is considered suitable for easy application to a wound site.

In a further embodiment, other vinyl-substituted polymers e.g. polysaccharides co-polymerized may be covalently attached to or incorporated into the gelatin hydrogel matrices of the present invention through SIPN technology (semi-interpenetrating polymer network) or a combination thereof. Especially high molecular weight components can be mechanically entrapped within the polymer network, such that covalent attachment is not always required. In a similar way other components which may add complementary properties to the gel can be utilized. These components may consist of molecules which have a known affinity for certain growth actors or wound healing-promoting substances. Examples of such components are those with affinity for heparin binding proteins, such as heparin or functional analogs of heparin such as heparan sulfate, chondroitin sulfate, dermatan sulfate, dextran sulfate or any other non-toxic polyanionic group displaying sufficient affinity for one or more of the molecular factors implicated in the wound healing process or monoclonal or polyclonal antibodies or microproteins that can be obtained through phage display and that have a high and selective affinity for molecular factors implicated in the wound healing process (see also previous application EP 95-59 GDP). When applied onto a wound, such affinity matrices have the potential to act as a reservoir for the accumulation and stabilisation of locally available endogenous growth factors or other wound repair stimulating factors. These factors may subsequently be gradually released, thus promoting healing of the injury. The potential of heparin-like molecules and similar polyanions to bind and stabilize certain growth factors is well known in the art. The following are but a few examples from the scientific literature discussing this subject. Volkin et al. have described the physical stabilisation of acidic FGF by different types of polyanions (Arch. Biochem. Biophys., 300, p.30–41, 1993; Biochim. Biophys. Acta 1203, p.18–2 , 1993). Tomoko et al. describe the stabilization of basic FGF with dextran sulfate (FEBS Letters, 306, p.243–246, 1992). Turnbull and Gallagher review the role of heparan sulphate as a functional modulator of fibroblast growth factor activity (Biochem. Soc. Trans. 21, 477–482, 1993). By the incorporation of such polyanionic compounds in the hydrogel matrices of this invention, the favourable biocompatibility and wound healing properties of the matrices may still further be improved.

Alternatively the components incorporated into or attached to the affinity matrix, may display an affinity for molecular factors that is high enough that binding can become a stable process. When applied onto a wound, such affinity GDP matrices have the potential to specifically sequester molecular factors that are detrimental to the wound healing process, such as factors that cause deregulated growth or hypertrophy or a superfluous formation of collagen. and that can cause the formation of keloids.

In the present invention we also disclose our discovery that gelatin hydrogel matrices of this invention constitutes an efficient and versatile material for the fabrication of slow or controlled release devices for the delivery of pharmacologically active substances. Peptide or polypeptide substances can be incorporated and subsequently efficiently released from the hydrogel matrices. This is demonstrated in Example 3, showing the efficient release of several iodinated polypeptides.

Pharmacologically active factors of interest can be incorporated in the hydrogel matrices of the present invention in several ways. The most preferred method is to add the factors prior to the cross-liking process. Therefore, an aqueous solution of the active agent is mixed with an aqueous solution of gelatin or vinyl-substituted gelatin at a temperature of about 37° C., followed by polymerisation of the vinyl-substituted gelatin, or by SIPN forming of gelatin with vinyl-substituted polysaccharides, or by co-polymerisation with vinyl-substituted polysaccharides. Thereafter, the resulting mixtures are allowed to cool. Since gelatin solutions are viscous, care should be taken that the different components are mixed thoroughly, so that a homogeneous distribution of the active agent in the gelatin hydrogel matrix is obtained. Another possibility is to incorporate the active factors in the gelatin hydrogel matrices of the present invention after the cross-linking process is completed, by means of a sorption procedure. Therefore, the gelatin hydrogel matrices are partially or completely dehydrated. This dehydration can be achieved by drying the matrices in an air stream, by lyophilisation, by organic solvent extraction or by any other suitable means resulting in removal of water from the matrix. Subsequently, the dehydrated matrices are soaked in an aqueous solution containing the active agent. During this soaking process, the matrices are rehydrated, at the same time absorbing part of the active agent.

One of the possible applications of the present invention lies in the fabrication of wound dressings containing one or more wound repair stimulating factors and/or a suitable antiseptic agent. Wound repair stimulating agents which are eligible for incorporation in such a wound dressing are for instance growth factors such as those belonging to the class of the EGF, FGF, PDGF, TGF-β, VEGF, PD-ECGF or IGF families. Another suitable agent would be a releasate from human platelets, which is for instance marketed by Curative Technologies Inc under the name Procuren. Also possible would be the incorporation of a conditioned medium, a lysate or an extract prepared from keratinocytes, such as disclosed in patent applications U.S. Pat. No. 9,106,161, (Oregon Univ.), EP88101576 (Eisinger), WO93/10217 (IG). Suitable antiseptic agents include antibiotics, antibacterial sulfamides or peptides, chinolones, antimycotics, etc., as far as they are suitable for topical use. Wound dressings containing wound repair promoting agents can be used for the treatment of wounds which are difficult to heal. Injuries which are eligible for such treatment include but are not limited to chronic ulcera, decubitus wounds and pressure sores, foot ulcers, corneal injuries, tympanic membrane perforations, surgical wounds, skin graft donor sites, burn wounds, etc. In the case of burn wounds, the wound dressings can be directly applied on a second or third degree burn. However, in case of extensive third degree burns, it is preferable to first graft the burn with meshed autologous skin. Application of the medicated gelatin hydrogel wound dressings of the present invention directly on top of this autologous meshed graft will stimulate the closure of the meshed graft intersticies, resulting in faster wound closure and concomitant reduction of infection risks and shortening of treatment time.

To facilitate application on the treatment site, the medicated gelatin hydrogel wound dressings of the present invention can be manufactured in different forms. For instance, sheet- or film-like dressings can conveniently be applied onto burn wounds, shallow ulcers, skin graft donor sites and other types of shallow wounds. To reduce fluid evaporation and dehydration of the dressing and the underlying wound, the dressing can be covered with a flexible membrane, the water permeability of which is chosen so as to obtain an optimal moisture level of the wound. It is also possible to manufacture multi-layered gelatin hydrogel laminates. Each layer of such a laminate can have different release properties and contain a different active substance. Upon application on the wound this will result in the controlled release of the incorporated factors from the subsequent layers, according to a predefined sequential and temporal programme. This programme will depend in part on the release properties and biodegradation of the different layers, their thickness and on the properties of the incorporated factors. Obtaining such a controlled delivery of multiple drugs is considered desirable because it is known that the wound repair process occurs in different stages, each of which requires the involvement of different factors. For instance, one stage of wound healing consists of the development of granulation tissue. This phase may be stimulated for instance by administration of PDGF or FGF. In a next phase, the wound is closed by an epithelialisation process, which may be stimulated by EGF. Inclusion of factors such as VEGF or PD-ECGF may optimize a process such as vascularisation which is often unsatisfactory and can be the underlying cause in chronic wounds such as ischaemic wounds. Which factor has to be released at which time point to obtain optimal healing results depends partly on the type of wound. It is also known that sometimes the wound healing process can be aberrant leading to the formation of persistently heavy scars or keloids. Such keloid formation is predisposed by two main factors. The first is the location of the scar and the second is the genetic background of the patient. It is therefore anticipated that keloid formation results from the atopic or superfluous presence of certain factors and that the presence of certain layers within the wound dressing can be used to sequester these unwanted factors. Other factors that can be sequestered comprise those that can lead to superfluous formation of collagen and/or elastin, thereby preventing phenomena such as skin contractions or keloid formation. It is one of the advantages of the present invention that programmed delivery of several drugs is possible using only one dressing, i.e. without having to change wound dressings.

In case of deeper wound cavities, such as some types of pressure sores or chronic ulcers, it may be more convenient to fabricate the medicated gelatin hydrogel wound dressings of the present invention in the form of microparticles, foams, pastes or other forms which are easily conformable to the wound shape. Microparticles may be fabricated according to any of the procedures known in the art, provided the activity of the incorporated active substances is not destroyed. To increase the shelf life of the medicated particles, it is also possible to lyophilize them. The resulting powder or granulate can be applied onto the wound either directly, in which case it will have the added benefit of adsorbing excess wound fluid, or it can be first rehydrated by incubation in a suitable aqueous solution. The medicated particles can also be formulated in a suitable excipient such as Vaseline, paraffin oil, etc. so as to obtain a paste which can for instance be used to fill a cavity.

In one of the embodiments of the present invention, the pharmacologically active substance is incorporated into affinity gelatin hydrogel matrices such as described above. In this case, the matrix contains also additional cross-linked, non-diffusible or otherwise immobilized compounds which have an affinity for the active substance. This results in a reduction of the release rate of the active agent and in some cases they may also stabilize the agent.

Following are but a few examples of such affinity ligands which may be incorporated into gelatin hydrogel matrices of the present invention.

One class is constituted by those molecules which display an affinity for heparin binding proteins, such as heparin or functional analogs of heparin such as heparan sulfate, chondroitin sulfate, dermatan sulfite, dextran sulfate or any other non-toxic polyanionic group displaying sufficient affinity for an incorporated heparin-binding factor. Examples of such factors include FGFs, HB-EGF, amphiregulin and betacellulin.

Another example of affinity ligands may consist of hydrophobic chains, which could retard the release of incorporated active agents with a hydrophobic nature. Incorporation of such chains in gelatin hydrogels of the present invention could be achieved for instance by the use of partially hydrophobized vinyl-substituted polysaccharides. These can be obtained for instance by partial esterification of dextran with fatty acids (e.g. caproic acid, stearic acid) followed by reaction with methacrylic acid anhydride of the thus obtained dextran esters.

It will be clear to the person skilled in the art that the fabrication of medicated wound dressings with controlled release properties is but one application of the present invention. Many other possible applications of the use of gelatin hydrogels of the present invention as a controlled release matrix can be envisaged. The following possibilities are intended only as examples and do not in any way limit the range of possible applications.

Gelatin hydrogen, of the present invention can for instance be used for the fabrication of devices for transdermal drug delivery. A gelatin hydrogel patch containing a transdermally deliverable drug can be attached to the skin, enabling a slow release of the drug over a prolonged time period. An occlusive film attached to such device can prevent the biopolymer from desiccation. In another application, gelatin hydrogel microparticles loaded with a particular drug can be injected intravenously, subcutaneously or intramuscularly. Equipped with a tagging system, such injected microparticles may be used for topical administration of compounds with which the microparticles were loaded. In principle, all drugs for which a slow release over a period ranging between a few days to a few weeks is desirable are eligible for incorporation in microparticles of gelatin hydrogels of the present invention. Examples include, but are not limited to, anticancer drugs, hormones, vaccines, contraceptives, cardiovascular drugs, neuroactive drugs etc.

Gelatin hydrogel films were prepared and exposed to LWUV-light (365 nm, 10 mW/cm$^2$), as described in example 2 A. After one week of hydrogel films storage at 4° C., the temperature dependence of the storage (elastic) modulus was determined by oscillatory shear deformation and temperature scan ranging from 16 to 50° C. (heating rate 1.75° C. min$^{-1}$) at constant frequency (1 Hz) and constant shear strain ($\gamma$=0.05, 1.88 mrad). Gelmod: methacrylamide-modified gelatin, gelmod+DMPA: methacrylamide-modified gelatin+ photoinitiator system.

Figure 2:
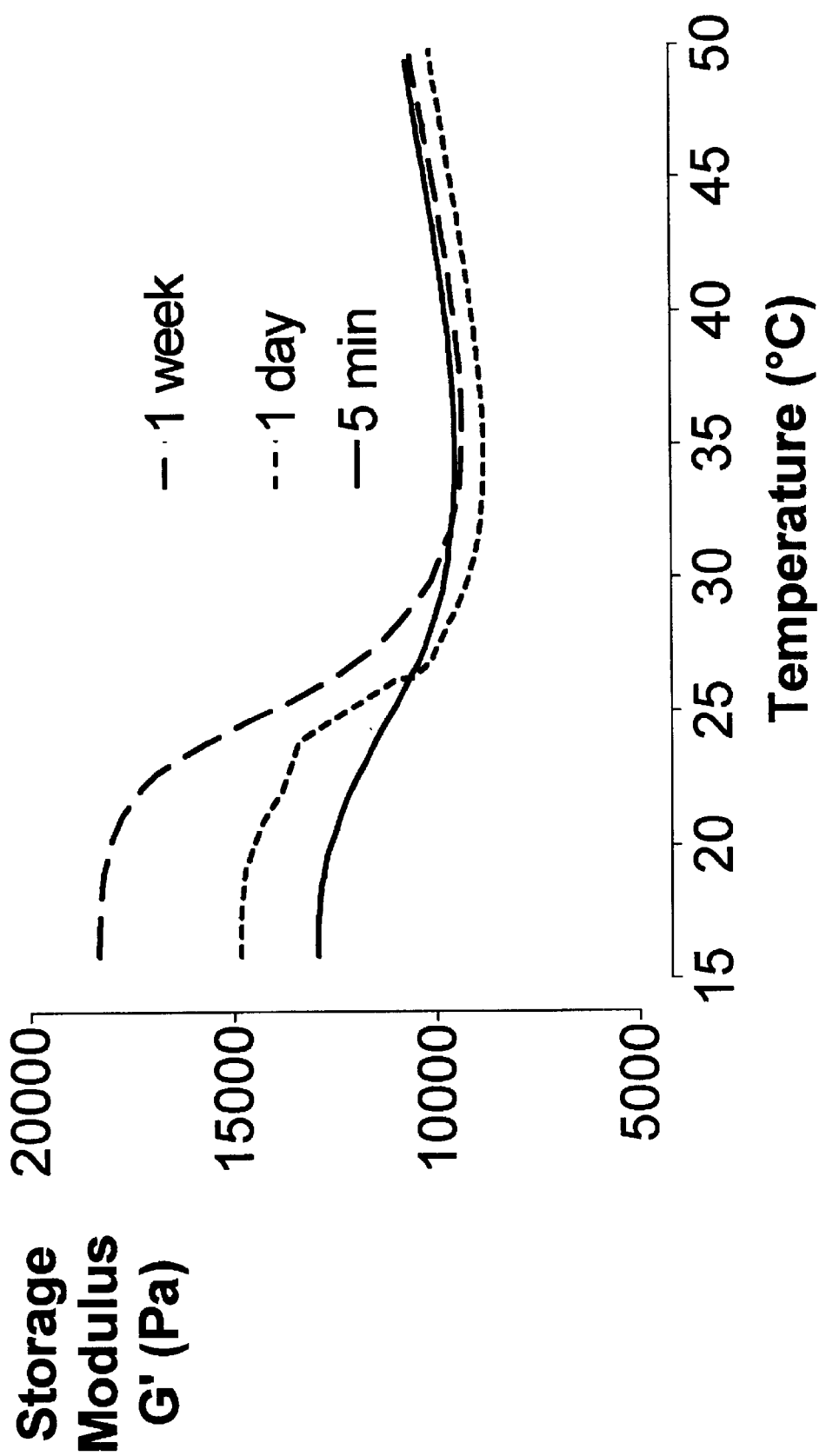

FIG. 2 Visco-elastic properties of cross-linked vinyl-modified gelatin hydrogel films upon increasing hydrogel storage time.

The temperature dependence of the storage (elastic) modulus was determined by oscillatory shear deformation and temperature scan ranging from 16 to 50° C. (heating rate 1.75° C. min$^{-1}$) at constant frequency (1 Hz) and constant shear strain ($\gamma$=0.05, 1.88 mrad).

Figure 3:
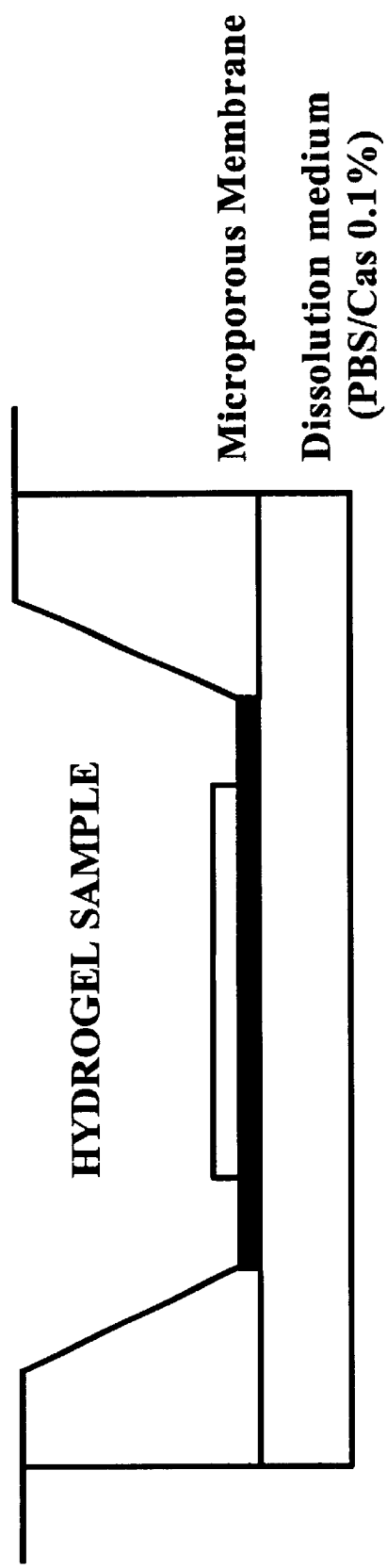

FIG. 3 Transwell-COL system for the release studies.

To allow the release of polypeptides by only one side of the hydrogel films, the hydrogel film samples were applied on a microporous collagen-treated membrane of a cell culture insert, and the volume of the extraction medium was adjusted so as to come in contact with the bottom face of the microporous membrane.

Figure 4A:
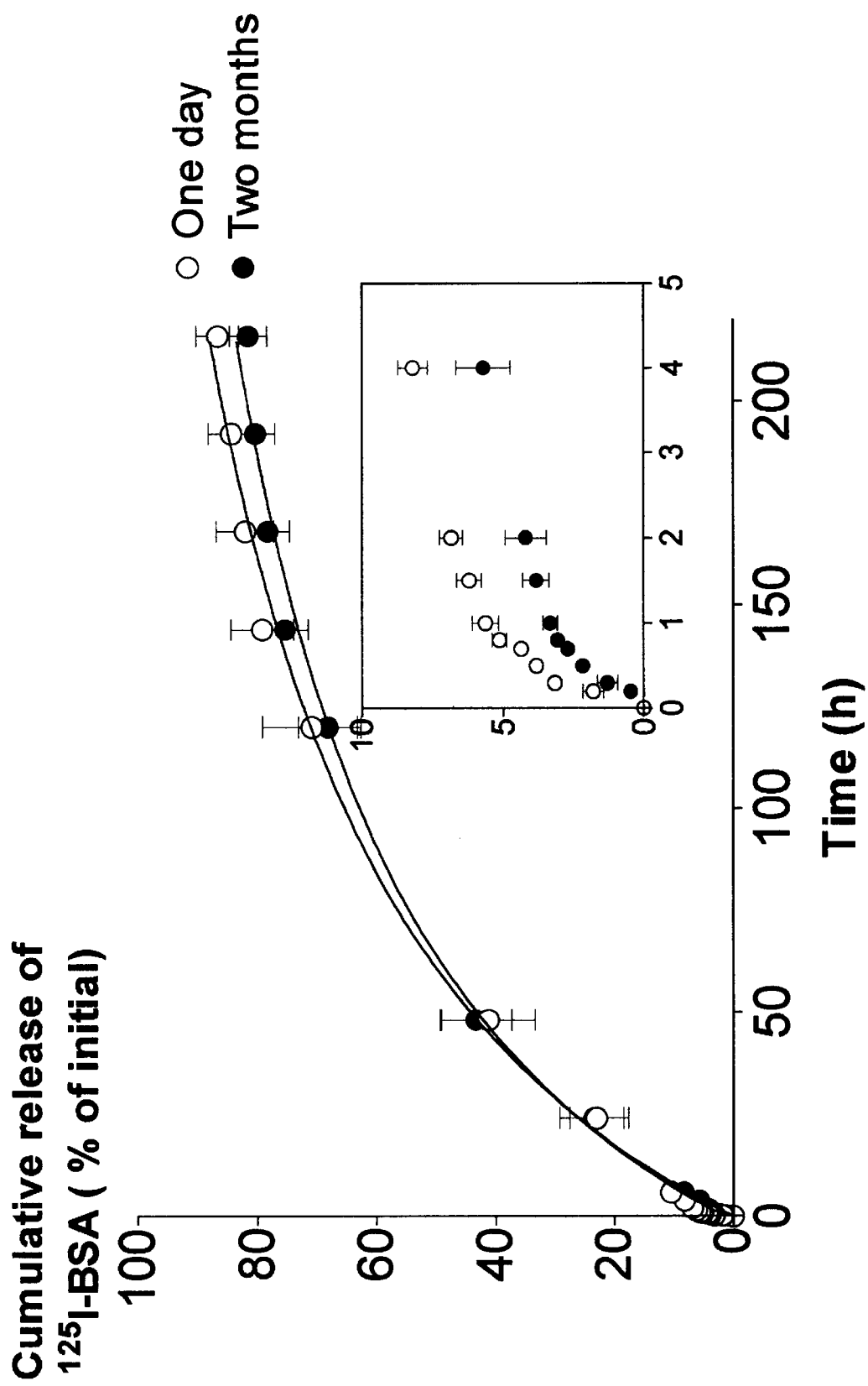
Figure 4B:
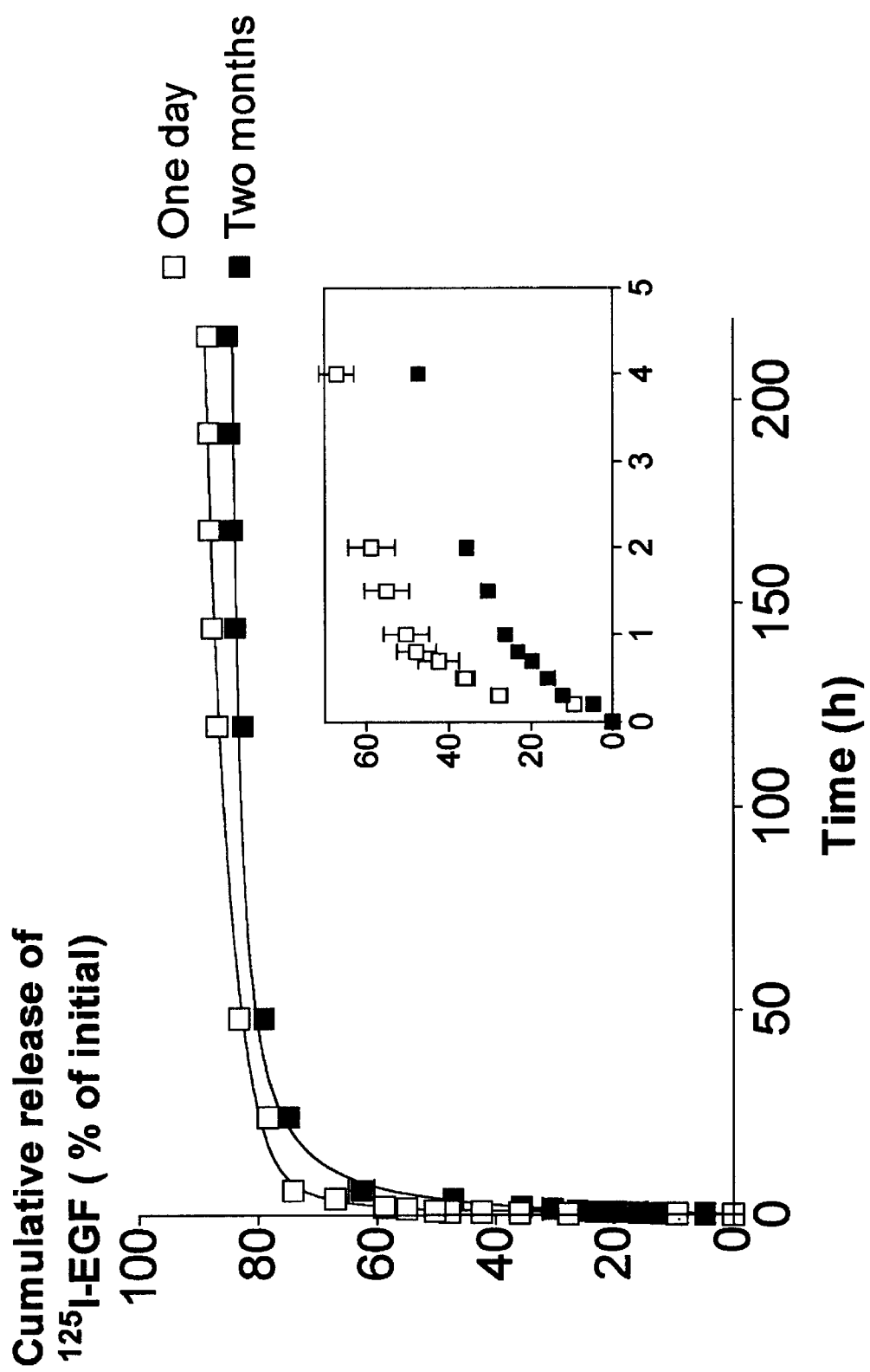

FIG. 4 Release of $^{125}$I-BSA (A) and $^{125}$I-EGF (B) from hydrogel films made of methacrylamide-modified gelatin with a degree of substitution of 60% (60% of the $\epsilon$-amino groups of gelatin were modified with vinylside groups) and prepared as described in Example 1. The same units apply for the inset.

Figure 5A:
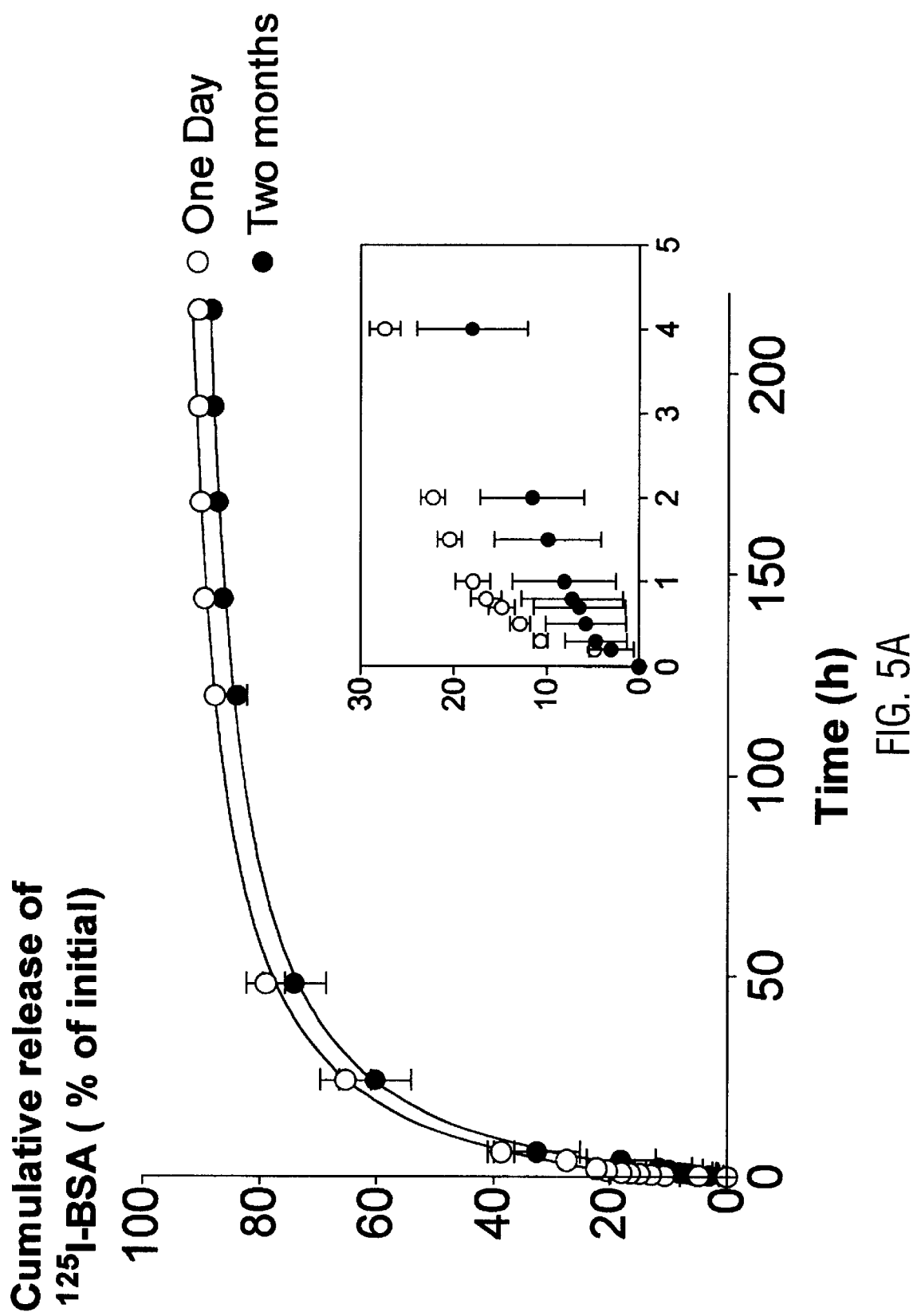
Figure 5B:
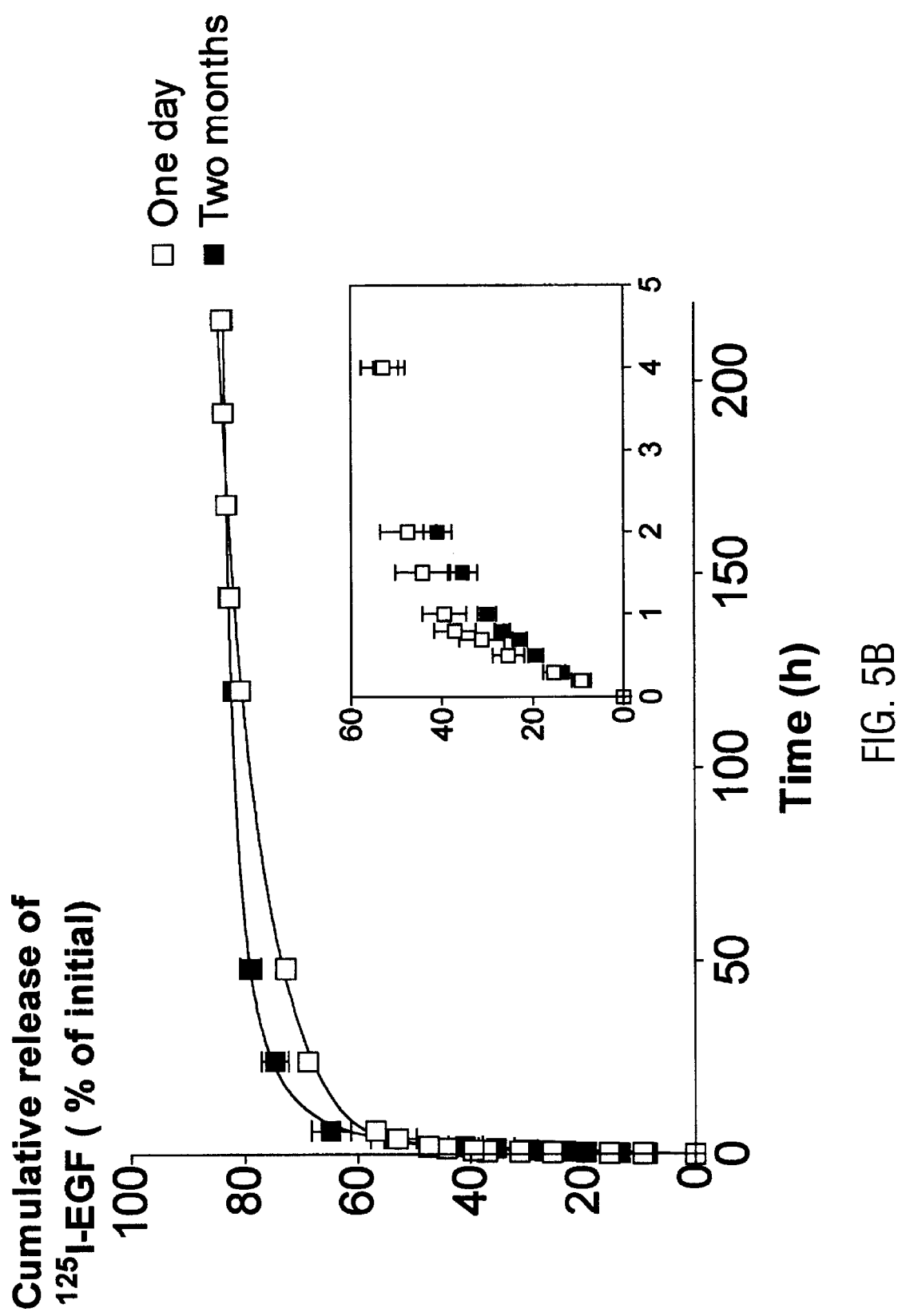

FIG. 5 Release of $^{125}$I-BSA (A) and $^{125}$I-EGF (B) from hydrogel films made of methacrylamide-modified gelatin with a degree of substitution of 60% (60% of the $\epsilon$-amino groups of gelatin were modified with vinylside groups) and acrylamide-modified dextran with a degree of substitution of 10% (10 vinylside groups per 100 glucoside units) and prepared as described in Example 1. The same units apply for the inset.

Figure 6A:
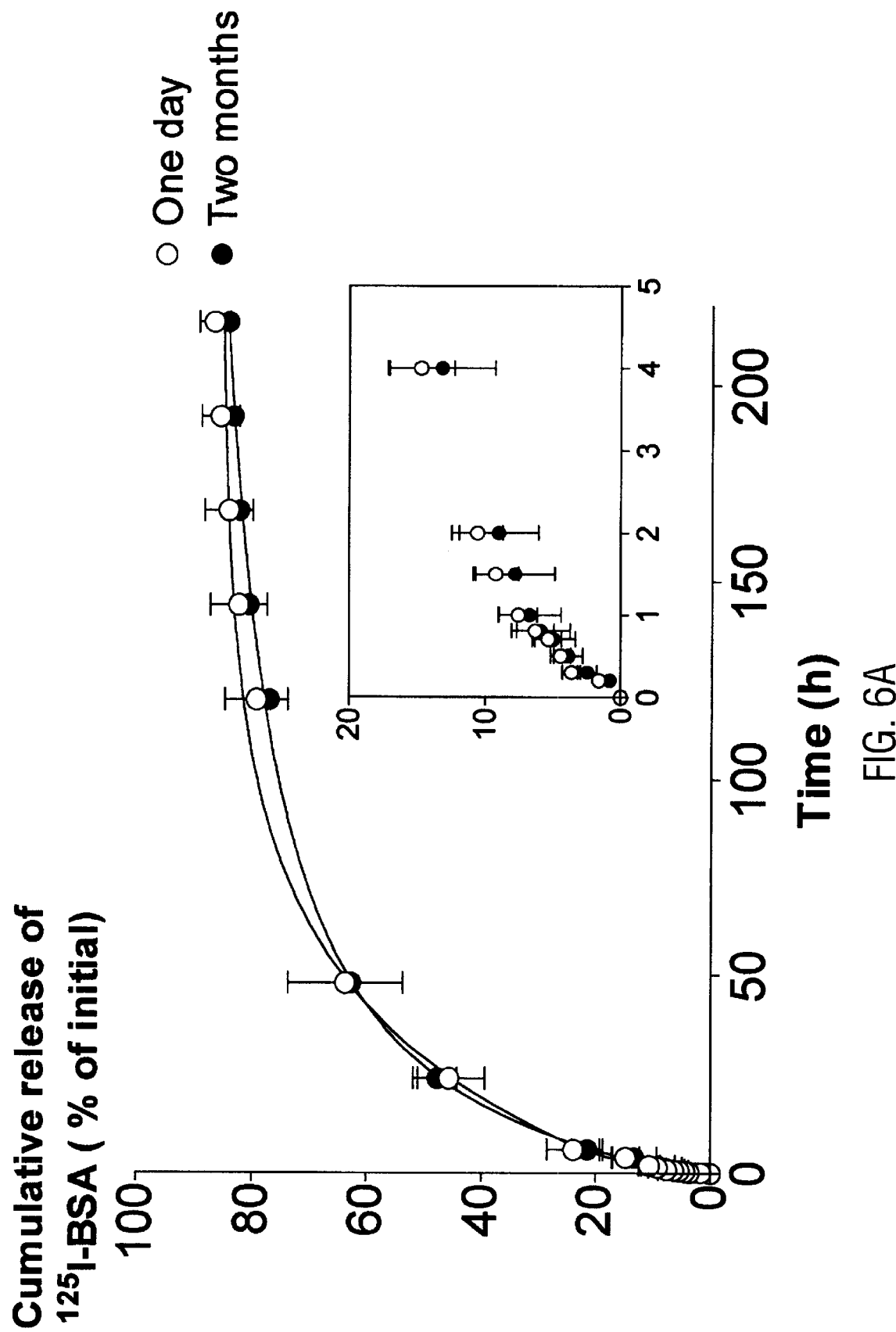
Figure 6B:
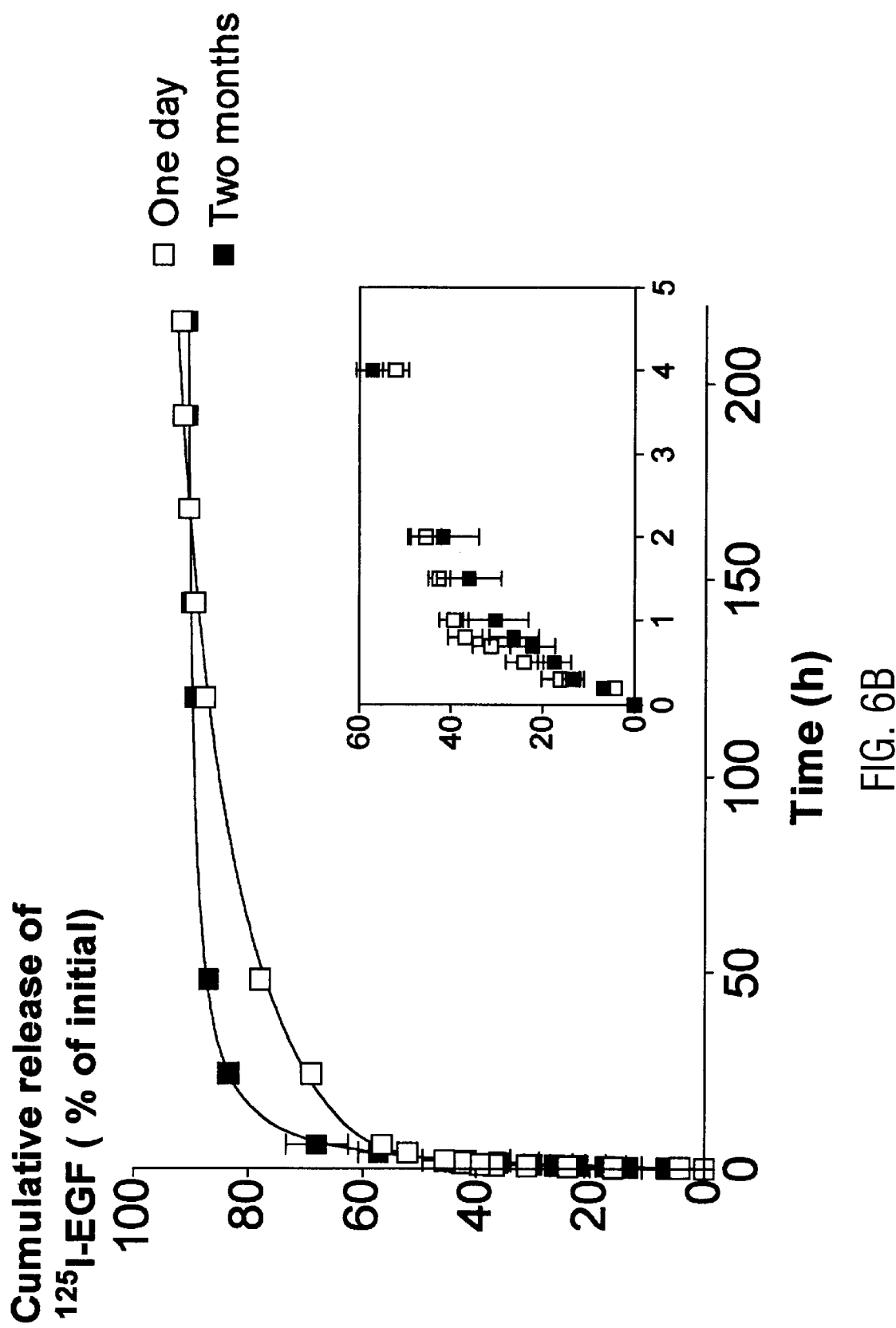

FIG. 6 Release of $^{125}$I-BSA (A) and $^{125}$I-EGF (B) from hydrogel films made of methacrylamide-modified gelatin with a degree of substitution of 60% (60% of the $\epsilon$-amino groups of gelatin were modified with vinylside groups) and methacrylate-modified dextran with a degree of substitution of 10% (10 vinylside groups per 100 glucoside units) and prepared as described in Example 1. The same units apply for the inset.

FIG. 7 Preparation of the vinyl-modified derivatives.

Methacrylamide-modified gelatin can be prepared by reaction of gelatin (Gel-NH$_2$) with methacrylic anhydride (A), Vinyl-modified dextran can be prepared by reaction of dextran (Dex-OH) with either 2-vinyl-4,4-dimethyl-2-oxalin-5-one (vinylazlacton) (B), or with methacrylic anhydride (C).

Figure 8:
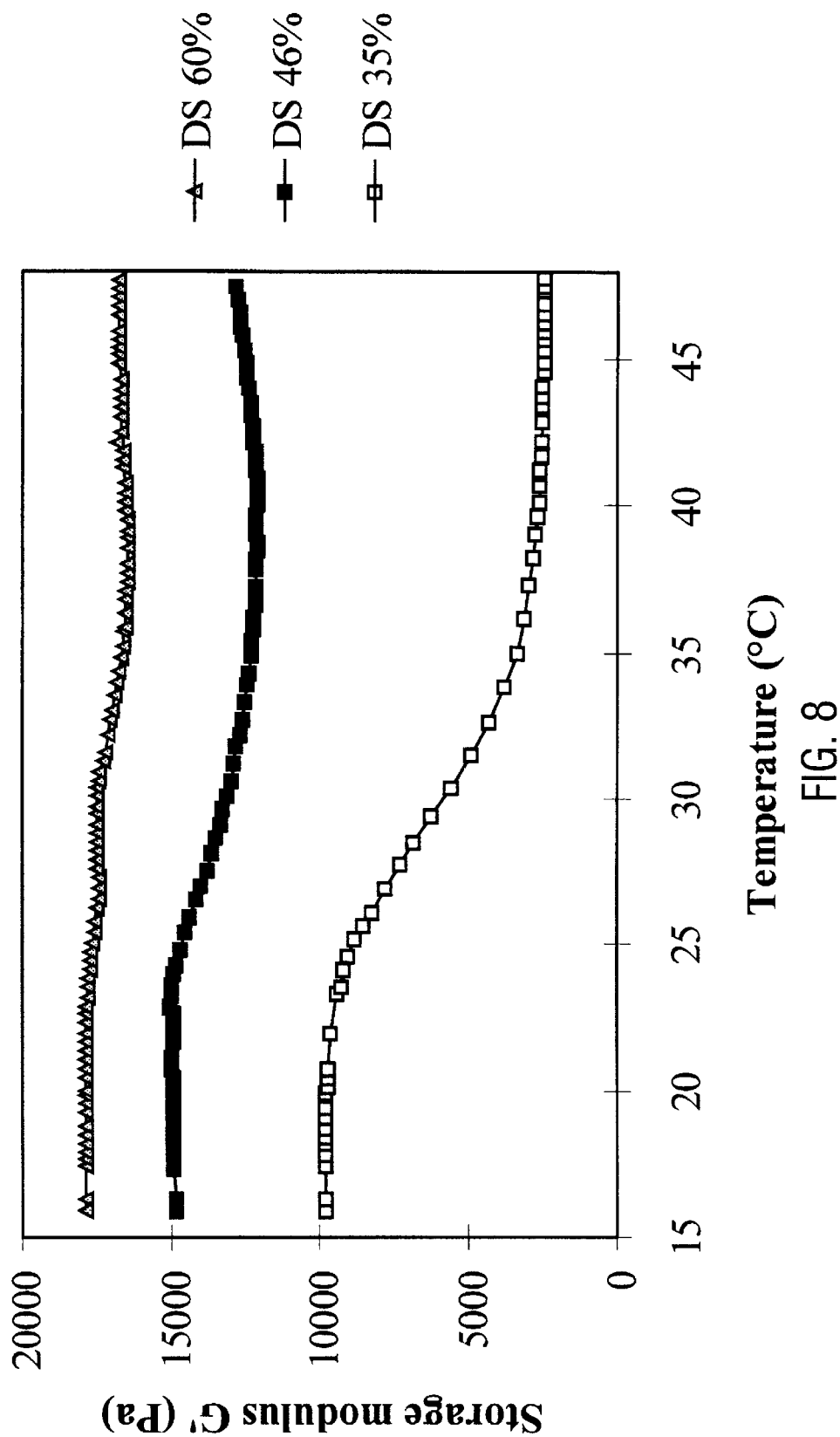
Figure 9:
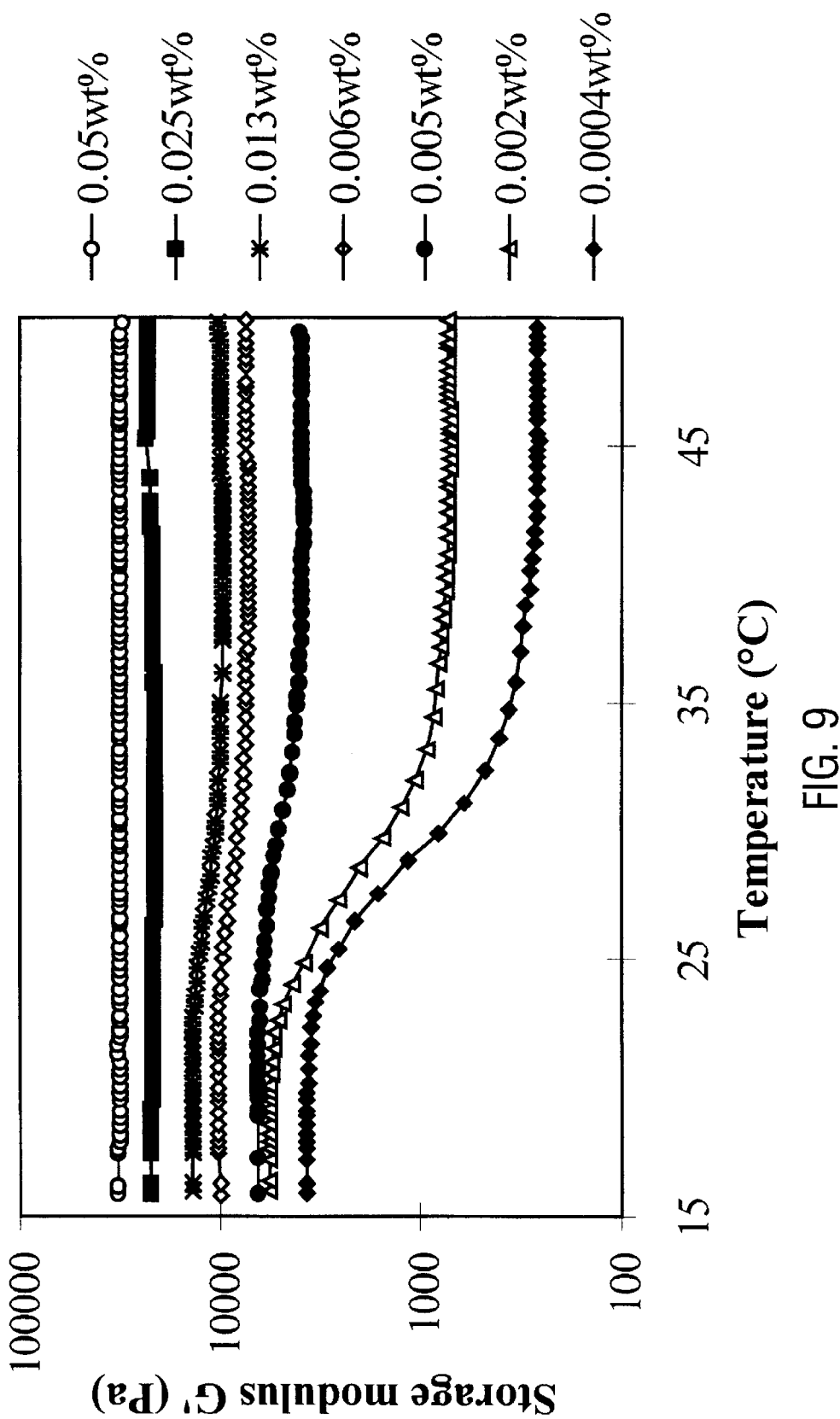
Figure 10:
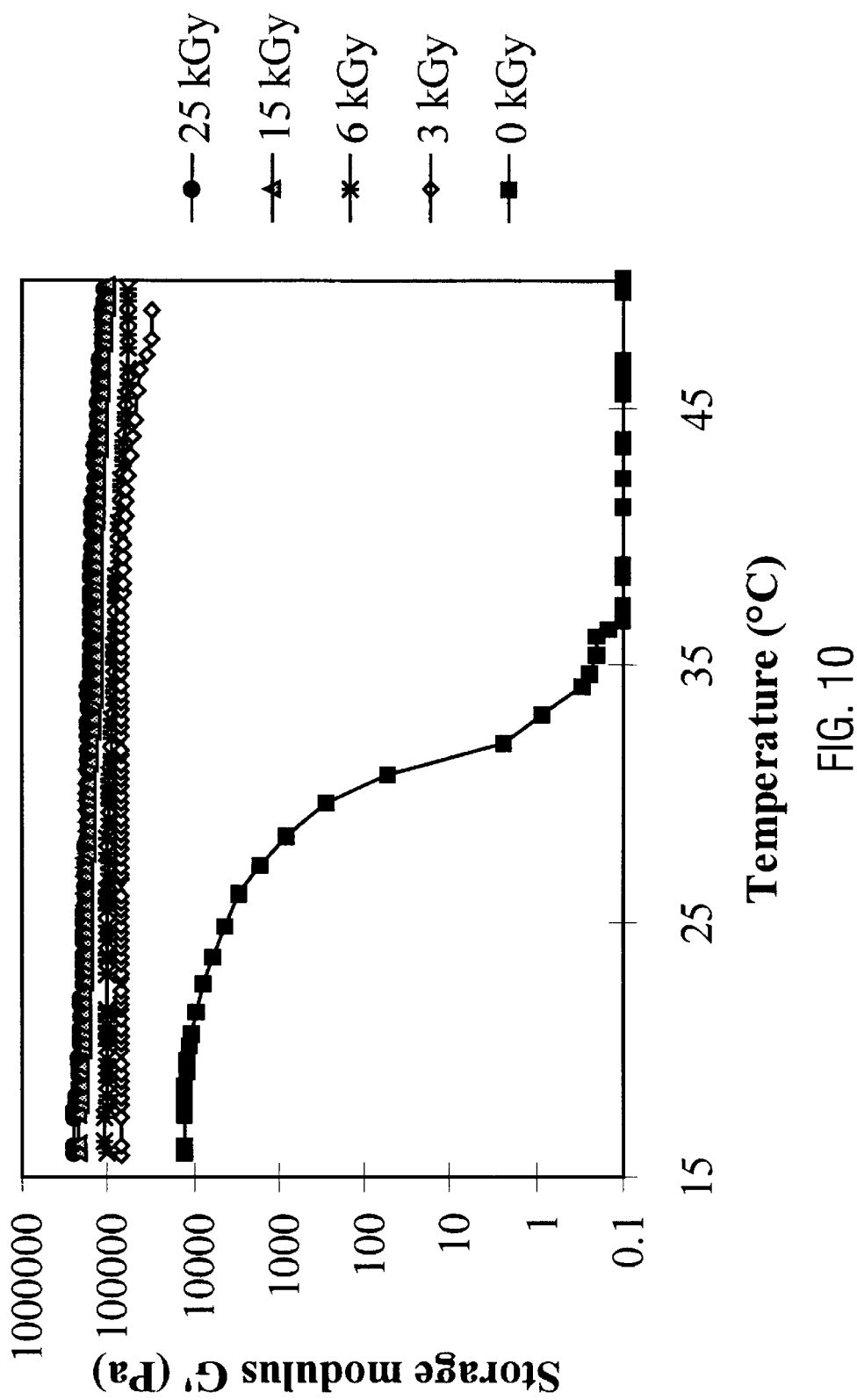

FIG. 8 Temperature dependence of the storage modulus G' of gelatin methacrylamide hydrogels, DS=35%, 46% en 60% with polymer concentration 15wt % in water; initiator concentration 0.006 wt % (Irgacure 2959) UV-exposure 30 min (365 nm, 10 mW/cm$^2$); storage temperature 4° C.; storage time after UV-irradiation 2 days; oscillatory shear deformation γ=0.05; frequency f=1 Hz FIG. 9 Temperature dependence of the storage modulus G' of gelatin methacrylamide hydrogels, DS=60% with polymer concentration 15 wt % in water; initiator concentration 0.0004 wt %→0.05 wt % (Irgacure 2959) UV-exposure 60 min (365 nm, 10 mW/cm$^2$); storage temperature 4° C.; storage time after UV-irradiation 2 days; oscillatory shear deformation γ=0.05; frequency f=1 Hz FIG. 10 Temperature dependence of the storage modulus G' of gelatin methacrylamide hydrogels, DS=60%, polymer concentration 15 wt % in water; γ-irradiation dosis 0, 3, 6, 15 and 25 kGy; storage temperature 4° C.; storage time before γ-irradiation 11 days; storage time after γ-irradiation 7 days; oscillatory shear deformation γ=0.05; frequency f=1 Hz FIG. 11 Temperature dependence of the storage modulus G' of gelatin methacrylamide hydrogels, DS=16%, 25 and 30% with polymer concentration 15 wt % in water; γ-irradiation dosis 6 kGy; storage temperature 4° C.; storage time before γ-irradiation 11 days; storage time after γ-irradiation 4 days; oscillatory shear deformation γ=0.05; frequency f=1 Hz

EXAMPLES

Example 1

Production of Gelatin Hydrogel Films
Preparation of Gelatin Methacrylamide

Gelatin methacrylamide can be prepared by reaction of gelatin with methacrylic anhydride (FIG. 7A). Ten g of gelatin, corresponding to about 3.28 nmol of ε-amino groups of lysine and hydroxylysine residues, are dissolved in 100 ml PBS-buffer (pH 7.4) and stirred at 50° C. After complete solubilization of gelatin, 0.5 ml methacrylic anhydride (3.35 mmol) are added. The mixture of gelatin and methacrylic anhydride is stirred for 1 hour at 40–50° C. Thereafter the mixture is dialysed against water during a few days at 40° C. and lyophihized. Evaluation of the content in free ε-amino groups of lysine and hydroxylysine residues present in the gelatin by the trinitrobenzene sulphonic acid method indicates that one gram of the methacrylamide gelatin obtained, still contains 0.284 nmol of free ε-amino groups. This evaluation allows to calculate that 55% of the ε-amino groups of the modified gelatin are still free and that 45% of the amino groups of the gelatin were modified.

Preparation of Acrylamide-modified Dextran

Vinyl-modified dextran can be prepared by reaction of dextran with 2-vinyl-4,4-dimethyl-2-oxalin-5-one (vinylazlacton) as seen in FIG. 7B. One gram of dextran (MW 40000) corresponding to 6.2 meq glucoside units is dissolved in 20 ml dimethyl sulfoxide (DMSO). Then 0.26 g (1.86 mmol) of vinylazlacton and 36.4 mg (0.3 mmol) 4-N,N dimethylaminopyridine (DMAP) are added to the dextran dissolved in DMSO and stred at 50° C. during 24 h. The polymer is isolated by precipitation in excess acetone. After drying and redissolving in water it is dialysed against water for two days at room temperature and freeze dried. NMR measurements indicate that a 30% vinyl substitution of dextran is achieved (30 vinylside groups per 100 glucoside units).

Preparation of Dextran Methacrylate

Vinyl-modified dextran can also be prepared by reaction of dextran with methacrylic anhydride (FIG. 7C). One gram of (6.2 meq glucoside units) of dextran (MW40000) is dissolved in 20 ml DMSO. To the dextran solution, 0.092 ml methacrylic anhydride (0.62 mmol) and 36.4 mg (0.3 mmol) DMAP are added. After stirring at 50° C. during 1 h, the polymer is precipitated in a large volume of a methanol: acetone mixture (1:1). The dry product is then redissolved in water and dialysed for two days at room temperature and freeze dried. The degree of substitution is measured by NMR experiment. A 10% vinyl substitution of dextran is achieved (10 vinyl side groups per 100 glucoside units).

Preparation of a Gelatin Hydrogel Film

Cross-linking of the methacrylamide-modified gelatin, or co-polymerization of gelatin methacrylamide with vinyl-substituted dextran, or cross-linking of vinyl-substituted dextran in the presence of gelatin, gelatin being physically entrapped in a semi-interpenetrating network, is performed in aqueous medium in the presence of radical initiators. The initiators can be a redox initiating system such as ammonium persulfate+N,N,N',N'tetramethylene diamine (1 μmol/gram gel) or a photo initiator such as 2,2-dimethoxy-2-phenylacetophenone (DMPA)+light treatment. For example, to prepare hydrogel films by radical cross-linking, vinyl-modified derivatives solutions (at 40° C.) containing DMPA as photo initiator, can be poured into a cast made of two glass plates separated by spacers of 1 mm thickness, and irradiated (10 mW/cm$^2$) at 365 nm for 10 min with a LWUV-lamp model VL-400L (Vilber Lourmat, Marne La Vallée, France). After removal of the glass plates a flexible 1 mm thick film is obtained which is water-insoluble.

Example 2

Visco-elastic Properties of Cross-linked Methacrylamide Modified Gelatin Films

Figure 1:
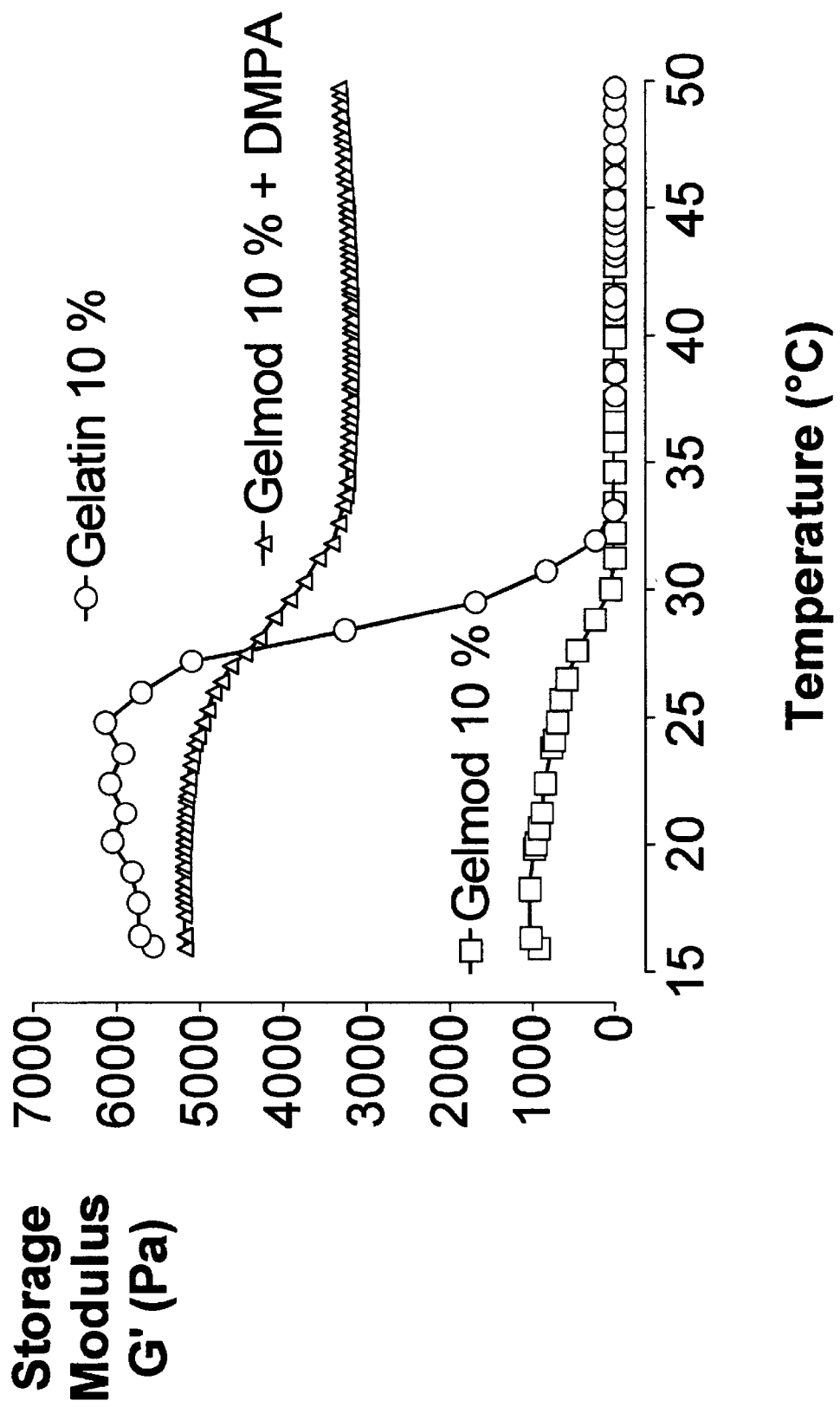
FIG. 1 Visco-elastic properties of gelatin, vinyl-modified gelatin and cross-linked vinyl-modified gelatin hydrogel films.

A) Characterization of the Mechanical Properties (Elastic Modulus) of Gelatin Methacrylamide Hydrogel Films The dynamic shear oscillation measurement at small strain were used to characterize the visco-elastic properties of cross-linked methacrylamide-modified gelatin hydrogel films. Methacrylamide-modified gelatin with a degree of substitution of 45% (45% of the ε-amino-groups of gelatin were modified with vinylside groups) was prepared as described in Example 1. Cross-linking of the methacrylamide-modified gelatin was performed in aqueous medium in the presence of 2,2-dimethoxy-2-phenylacetophenone (DMPA) used as photoinitiator. Gelatin methacrylamide (1 g) was dissolved in 10 ml (10 wt %) of a phosphate buffer saline solution (pH 7.4) warmed at 40° C. DMPA (6 mg) was added to the methacrylamide-modified gelatin solution and stirred at 40° C. for 1 min. The warm mrixture was then poured into a cast made of two glass plates separated by 1 mm-thick spacers and exposed for 10 min to the light (365 nm, 10 mW/cm$^2$) of a LWUV lamp model VL-400L. For the purpose of comparison, and to allow the distinction between the respective contribution of the physical and chemical cross-linking to the hydrogel elastic modulus, non-cross-linked gelatin hydrogel films and methacrylamide-modified gelatin hydrogel films were prepared in the absence of photo initiator (DMPA). For the gelatin hydrogel preparation, one g of gelatin was dissolved in 10 ml (10 wt %) of a phosphate buffer saline solution (pH 7.4) warmed at 40° C. and for methacrylamide-modified gelatin hydrogels, one g of methacrylamide-modified gelatin was dissolved in 10 ml (10 wt %) of a phosphate buffer saline solution (pH 7.4) warmed at 40° C.; both solutions were separately poured into casts made of two glass plates separated by 1 mm thick spacers. The hydrogel films were kept at room temperature for one hour, and thereafter stored at 4° C. for one week. The rheological measurements at oscillatory shear deformation were carried out with a $CSL^2$ Rheometer (TA Intruments) using parallel rough plates of 40 mm diameter and plate-to-plate distance of 800 μm. The temperature dependence of the storage (elastic) modulus was determined by oscillatory shear deformation and temperature scan ranging from 16 to 50° C. (heating rate 1.75° C. $min^{-1}$) at constant frequency (1 Hz) and constant shear strain ($\gamma=0.05$, 1.88 mrad). The temperature dependence of the storage (elastic) modulus G' of the hydrogel films is shown in FIG. 1. Gelatin hydrogel films were formed by physical gelation only and showed high G' values below the melting point of gelatin. When the temperature was increased above the gelatin melting point (sol-gel transition temperature: 28° C.–30° C.) the elastic modulus dropped rapidly to very low values due to the breakdown of the gelatin physical networks Methacrylamide-modified gelatin hydrogels, prepared wihout the addition of a photoinitiator, showed only low G' values, even below the sol-gel transition temperature indicating that poor physical network can be formed when velatin is modified with methacrylamide side groups. Above the sol-gel transition, the elastic modulus decreased rapidly to very low values, indicating that in the absence of photoinitiator, no chemical cross-linking was formed By contrast, the light treatment of DMPA-containing methacrylamide-modified gelatin solutions resulted in the production of a hydrogel film with high storage modulus (G') values, both below and above the melting point of gelatin, indicating that the presence of a photoinitiator system together with the light treatment induced a hydrogel chemical cross-linking. It was concluded that the mechanical properties (e.g. the elastic modulus) of the cross-linked methacrylamide gelatin films result from both the chemical cross-linkage and the physical structuring of methacrylamide-modified gelatin. It was also concluded that cross-linked methacrylamide-modified hydrogel films with appropriate mechanical properties for the fabrication of wound dressings can be produced.

B) Characterization of the Mechanical Properties (Elastic Modulus) of Gelatin Methacrylamide Hydrogel Films Upon Increasing Hydrogel Storage Time The storage modulus of cross-liked methacrylamide-modified gelatin hydrogel films was evaluated using oscillation test measurements at small deformation. Methacrylamide modified gelatin with a degree of substitution of 60% (60% of the ε-amino groups of gelatin were modified with vinylside groups) was prepared as described in Example 1. Cross-linking of the methacrylamide-modified gelatin was performed in aqueous medium in the presence of DMPA, used as photoinitiator. Methacrylamide-modified gelatin (1.5 g) was dissolved in 10 mm (15 wt %) of a phosphate buffer saline solution (pH 7.4) warmed at 40° C. DMPA (6 mg) was added to the methacrylamide-modified gelatin and stirred at 40° C. for 1 min. The warm mixture was then poured into a cast made of two glass plates separated by 1 mm-thick spacers and exposed for 10 min to the light (365 nm, 10 $mW/cm^2$) of a LWUV lamp model. The cross-linked hydrogel films were kept at room temperature for one hour, and thereafter stored at 4° C. for various time periods. The theological measurements at oscillatory shear deformation were carried out with a $CSL^2$ Rheometer (TA Instruments) using parallel rough plates of 40 mm diameter and plate-to-plate distance of 800 μm. The temperature dependence of the storage (elastic) modulus was determined by oscilatory shear deformation and temperature scan ranging from 16 to 50° C. (heating rate 1.75° C. $min^{-1}$) at constant frequency (1 Hz) and constant shear strain ($\gamma=0.05$, 1.88 mrad). The temperature dependence of the storage (elastic) modulus G' of a hydrogel film consisting of cross-linked methacrylamide-modified gelatin stored for different time periods is shown in FIG. 2. The hydrogel mechanical properties (e.g. the elastic modulus) result from the physical relation of the gelatin component and from the chemical cross-linking of the vinyl-modified gelatin. The temperature scan of the hydrogel specimens below and above melting point of gelatin allows to identify the respective contribution of the chemical and physical cross-linkage to the hydrogel elastic modulus. The light treatment of methacrylamide-modified gelatin and DMPA mixtures resulted in the production of a hydrogel films with high storage modulus (G') values below and above the melting point of gelatin, indicating the formation of chemical bonds in the gelatin hydrogel films. Upon increasing hydrogel film storage time, the G' values increased in the temperature range below 25° C., but remained constant in the temperature range above 25° C., indicating that the increase in the hydrogel storage modulus, upon increasing storage time, resulted only from an increase of the contribution of the physical structuring of gelatin chain. After one or two weeks of hydrogel storage, the G' values were stabilized, indicating that after a hydrogel maturation period, cross-linked methacrylamide-modified gelatin hydrogel films with stable mechanical properties (elastic modulus) can be obtained.

Example 3

Controlled Release of $^{125}$I-radiolabelled Polypeptides (EGF and BSA) from Cross-linked Gelatin Hydrogel Films Preparation of the Films Cross-linked gelatin hydrogel films containing the iodinated factors were prepared using similar procedures as described above, the polypeptides being added to gelatin or modified gelatin before hydrogels cross-linking. The gelatin hydrogels contained 0.02% thimerosal, as preservative. The concentration of iodinated test proteins in the gelatin hydrogel matrix was approximately 5 μg/ml.

Release Testing Using a Wound-mimicking System

For the evaluation of the release kinetics of controlled delivery wound dressings, an elution test system where the dressing sample is immersed in the extraction fluid under continuous agitation is not ideal. Since this kind of elution is carried out by means of an active extraction procedure, the release, in such a system, is much faster than would be observed in a wound. Shinde and Erhan (Bio-Med. Mat. Eng. 2: pp. 127–131, 1992) have reported such a kind of system for determining the release properties of insulin-loaded flexibilized gelatin films. We have adopted an alternative test system which mimics the wound situation. To quantify the release of polypeptides from gelatin hydrogels films, the release system shown in FIG. 3 was adopted. Samples (1.3 $cm^2$) of the gelatin hydrogel films were placed on a microporous collaglen-treated membrane (3 μm pore diameter) of a Costar's Transwell-COL cell culture chamber insert, itself placed in a well of a 6-well plate. The volume of the dissolution medium (1 ml of PBS containing 0.1% casein and 0.02% thimerosal) was adjusted so as to come in contact with the bottom face of the microporous membrane. Therefore, the hydrogel incorporated compounds were released by only one face of the gelatin hydrogel samples. This kind of release system was used in order to mimic conditions prevailing in an open wound, and to provide a more realistic assessment of release kinetics than a simple immersion system in which incorporated material would have been solubilized more rapidly. To simulate the wound conditions more closely, the release test was carried out in a thermostatized incubator at 37° C. At particular time points, the 1 ml extraction fluid was removed and replaced with 1 ml fresh fluid. To quantify the amount of labelled protein released, the radioactivity present in the removed extraction liquid samples was measured in a gamma-counter. To additionally evaluate the stability upon storage of the protein-loaded gelatin hydrogel films, release profiles were determined in films which had been stored at 4° C. for one day and two months. Extraction liquid samples were stored at −70° C. At the end of the release experiment, all the extraction liquid samples were thawed and were first precipitated with TCA prior to the radioactivity measurements, to be sure that only protein-associated radioactivity was quantified. At the end of the experiment, residual radioactivity was also determined in the gelatin hydrogel discs and in the Transwell-COL filter. The release kinetics of $^{125}$I-BSA (MW: 68 kDa) and $^{125}$I-EGF (MW: 6 kDa) from hydrogel films of various composition are shown in FIGS. 4, 5 and 6. After one day or two months of hydrogels storage, all the hydrogels evaluated displayed sustained release of polypeptides up to 9 day incubation. After this period of incubation, 80–90% of both polypeptides were released in the extraction medium. The release kinetics were characterized by a burst release which was followed by a plateau release. Although, $^{125}$I-EGF was more rapidly released than $^{125}$I-BSA, the results confirm that also for larger proteins release occurs with high efficiency and according to kinetics which are favourable for application in medicated wound dressings. Also, the stability of the matrix proves to be sufficient to allow prolonged storage, since the hydrogel storage has no or minor effect on the release kinetics. The new hydrogels, made of vinyl-derivatives of gelatin and dextran, were found to be an appropriate release system for medium-term sustained delivery of polypeptides.

Example 4

Influence of the Degree of Substitution on Gelatin Methacrylamide Gels.

Materials and Methods

Gelatin type B (G-9382, lot 26H0347) from Sigma is prepared by alkaline treatement of bovine skin. The gel strength is 225 Bloom.

Methacrylic anhydride (MAA) was obtained from Aldrich and was used as received. 1-(4-(2-Hydroxyethoxy)-phenyl)-2-hydroxy-2-methyl-1-propane-1-one (Irgacure® 2959) was obtained from Ciba.

Trinitrobenzene sufonic acid was purchased from Serva and acetyllysine from Bachem. Dialysis Membranes Spectra/Por®1(MW6000–8000) were obtained from Polylab (Antwerpen, Belgium).

Preparation of Gelatin Methacrylamide 100 g of gelatin (32.8 mmol of ε-aminogroups of lysine and hydroxylysine ) is dissolved in 1 liter phosphate buffered saline (PBS,pH 7.4) and stirred at 50° C. After complete solubilization of gelatin, 10 ml methacrylic anhydride (67.1 mmol) is added. The reaction mixture is stirred for 1 hour at 40–50° C. Thereafter the mixture is diluted with one liter of water and dialysed against water during 1 day at 40° C. and freeze dried.

Gelatin methacrylamide with lower degrees of substitution can be prepared by reducing the amount of methacrylic anhydride.

The determination of free amino groups in modified gelatin is measured by the trinitrobenzene sulfonic acid (TNBS) method. (Habeeb, Anal. Biochem., 14, 328–336, 1966) One ml of the proteine solutions (gelatin or gelatin methacrylamide in water) is mixed with 1 ml NaHCO$_3$ buffer (pH 8.5)(0.05M) and 1 ml TNBS solution (0.1%). The mixtures are covered from light and kept at 37° C. during 2 hours. Then 0.5 ml warm HCl (1N) is added and the absorbance is measured at 345 nm. All samples are prepared in triplate. This UV-method is performed upon a calibration curve of acetyllysine. Evaluation of the percentage of the remaining free ε-aminogroups after modification of the gelatin allows to calculate the degree of substitution (DS) of gelatin methacrylamide.

Reaction of gelatin with an excess of methacrylic anhydride leads to gelatin methacrylamides with degree of substitution up to 70% while reaction with one equivalent of anhydride only leads to modification of 46% (46 vinylside groups per 100 ε-aminogroups in the initial gelatin).

Preparation of Hydrogel Films

A LWUV lamp model VL-400L (Vilber Lourmat, Marne La Vallée) with flood 365 nm is used to irradiate the samples.

The reological measurements at oscillatory shear deformation on the hydrogels are carried out with a CSL$^2$ Rheometer (TA Instruments) using parallel rough plates of 40 mm diameter and a plate-to-plate distance of 800 µm. The temperature dependence of the storage (elastic) modulus is determined by oscillatory shear deformation and temperature scan in the range from 16 to 50° C. (heating rate 1.75° C. min$^{-1}$) at constant frequency (1 Hz) and constant shear strain (γ=0.05, 1.88 mrad).

Cross-linking of the methacrylamide-modified gelatin is performed in aqueous medium in the presence of a photo-initiator (Irgacure® 2959). 1.5 g gelatin methacrylamide is dissolved in a 10 ml (15 wt %) initiator solution (0.006 wt %) at 40° C. The warm mixture is then poured into a cast made of two glass plates seperated by spacers of 1 mm thickness. The hydrogel solution containing the UV-initiator is then exposed to LWUV-light (365 nm, 10 mW/cm$^2$) during 30 minutes at 30° C. After removal of the glass plates a flexible 1 mm thick transparant film is obtained which is water insoluble.

Influence of the Degree of Substitution on Gelatin Methacrylamide Gels.

The methacryiamide-gelatin (gelmod) hydrogels are prepared as described above. Hydrogel films containing gelatin with a different number of vinylside groups are evaluated by rheological measurements at oscillatory shear deformation. The degree of substitution (DS) is defined as the percentage of ε-aminogroups that are modified into a vinylgroup and is determined by the Habeeb method (TNBS). The DS has an appreciable impact on the storage modulus G' above 30° C., the chemical cross-linkage is thus strongly influenced by the number of reactive vinylside groups. Modified gelatin gels with DS of 35% or smaller show a large drop in storage modulus. The constitution of chemical cross-links in the low substituted gels (<35%) is neglectible. To obtain strong chemically cross-linked hydrogels gelatin methacrylamide with DS of about 46% are appropriate (see FIG. 8).

Example 5

Influence of the Initiator (IRGACURE® 2959) Concentrations

The methacrylamide-gelatin (gelmod) hydrogels are prepared as described in example 4. The temperature dependence of the storage modulus is strongly influenced by the initiator concentrations in the gel. An extensive drop of G' is observed when less than 0.002 wt % initiator-solution (0.21 mg Irgacure® 2959 per 10 ml polymer solution) is used. Hydrogels with 0.003 wt % initiator solution or more, show a higher storage modulus at high temperature and are therefore more densely chemically cross-linked. The mechanical properties of gelatin-methacrylamide hydrogels increases with higher initiator concentration. Although when concentrations higher than 0.025 wt % are applied, the hydrogels turn hard and brittle (see FIG. 9).

Example 6.
Effect of Irradiation Dosis on Gelatin Methacrylamide Gels

The effect of different irradiation dosis on the viscoelastic properties of gelatin methacrylamide hydrogels was evaluated. Gelatin methacrylamide with high degree of substitution (DS 60%) is used to prepare the tested films. The methacrylamide-gelatin (gelmod) hydrogels are prepared as described in example 4. The hydrogel films are irradiated in their cast (between glassplates) at room temperature. A strong chemical cross-linking occurs during radiation and hard but brittle hydrogels are obtained. Even with low dosis 3 kGy, a very high storage modulus G' is measured (FIG. 10). For wound dressing applications a more elastic hydrogels is needed, irradiation of gelatin-methacrylamide with lower degree of substitution is recommended.

Example 7
Effect of 6 kGy Dosis on Gelatin Methacrylamide Gels with Different Degree of Substitution.

Gelatin hydrogels with low degree of substitution are irradiated, in order to obtain less brittle materials as discussed above. The methacrylamide-gelatin (gelmod) hydrogels are furthermore prepared as described in example 4.

An extensive drop of G' is observed (FIG. 11) when gelatin methacrylamide with degree of substitution of 16% is irradiated (6 kGy) due to melting of not chemically cross-linked polymer. Physical relation of gelatin melts above 30° C. A more dense chemically cross-linked hydrogel is obtained with degrees of substitutions above 25% and strong but elastic hydrogels are formed, even at temperatures above the melting point of gelatin.

What is claimed is:

1. A composition containing a biopolymer matrix comprising constituents selected from the following:
    a. a methacrylamide modified gelatin and a polysaccharide, wherein the gelatin is modified with methacrylamide side groups which are capable of being radically cross-linked; or
    b. a gelatin and a vinyl-substituted polysaccharide, wherein the polysaccharide is modified with vinyl side groups which are capable of being radically cross-linked; or,
    c. a methacrylamide modified gelatin and a vinyl-substituted polysaccharide wherein the gelatin has been modified with methacrylamide side groups which are capable of being radically cross-linked and the polysaccharide has been modified with vinyl side groups which are capable of being radically cross-linked;
wherein the respective matrix constituents are physically entrapped in the matrix, after radically induced cross-linking polymerization or radically induced cross-linking copolymerization, so that they form a semi-interpenetrating network.

2. A composition according to claim 1, wherein the biopolymer matrix further comprises one or a mixture of two or more of the following compounds:
    a polysulfated oligo- or polysaccharide or fragments thereof;
    a biocompatible polyanion which has the capacity to bind heparin-binding growth factors;
    a proteoglycan containing glycosaminoglycan chains capable of binding to heparin-binding growth factors;
    a functional analogue of heparin which binds or stabilizes heparin-binding growth factors;
    a monoclonal or polyclonal antibody or a microprotein wherein said antibody or microprotein has a high and selective affinity for molecular factors that can modulate the wound healing process, and wherein said microprotein can be obtained by phage display;
    a therapeutically effective amount of a drug;
    compounds having substantial affinity for the incorporated drug, so as to slow down the release of the drug from the matrix and/or stabilizing the drug.

3. A composition according to claim 1 wherein said matrix is in the form of a hydrated or dry film, or a hydrated or dry foam, or hydrated or dry microbeads, or a dry powder, or hydrated or dry fibers which may be fabricated into a woven or non-woven tissue.

4. A composition according to claim 1, wherein said matrix is covered with a semipermeable film, with a permeability chosen so as to control the humidity of the wound covered with said biopolymer matrix.

5. A controlled or slow release device for releasing drugs or vaccines comprising a composition according to any one of claims 1 to 3 for transdermal drug delivery.

6. A controlled or slow release device comprising microparticles of a composition according to any one of claims 1 to 3 loaded with a drug or a vaccine which can be injected intravenously, subcutaneously, or intramuscularly.

7. A controlled or slow release device according to claim 5, wherein said matrix is covered with an occlusive or semipermeable film, to prevent desiccation of said matrix, or to control delivery of said drug or vaccine.

8. A wound dressing comprising a composition according to any of claims 1 to 3 or 4.

9. The wound dressing of claim 8 used for treating one of the following diseases:
    skin wounds (including burns, refractory or chronic ulcers, diabetic foot ulcers, necrotic and sloughy wounds, surgical wounds, decubitus ulcers and pressure sores, and ischaemnic wounds),
    cicatrization and keloid formation,
    necrotization of wound surrounding tissues,
    skin contractions,
    excess exudate or slough formation,
    corneal wounds or defects,
    post-surgical treatment after tympanic membrane reconstructions, or other middle ear reconstructions,
    chronic otorrhea, and
    dermatological disorders.

10. The composition of claim 1, wherein a methacrylamide modified gelatin is copolymerized with a vinyl-substituted polysaccharide.

11. The composition of claim 1 or 10, wherein said polysaccharide is vinyl-substituted dextran.

12. The composition according to claim 2, wherein the polysulfated oligo- or polysaccharide is selected from one or more of the following: heparin, heparin sulfate, chondroitin sulfate, dermatan sulfate, and dextran sulfate.

13. The composition of claim 1 wherein a gelatin is polymerized with a vinyl-substituted polysaccharide.

14. The composition of claim 1 wherein a methacrylamide modified gelatin is polymerized with a polysaccharide.

15. A biopolymer matrix produced by a process comprising:
    (a) providing a solution comprising:
        (i) a methacrylamide modified gelatin and a polysaccharide, wherein the gelatin is modified with methacrylamide side groups which are capable of being radically cross-linked; or (ii) providing a solution comprising a gelatin and a vinyl-substituted polysaccharide, wherein the polysaccharide is modified with vinyl side groups which are capable of being radically cross-linked; or, (iii) providing a solution comprising a methacrylamide modified gelatin and a vinyl-substituted polysaccharide wherein the gelatin has been modified with methacrylamide side groups which are capable of being radically cross-linked and the polysaccharide has been modified with vinyl side groups which are capable of being radically cross-linked; and (b) radically inducing cross-linking polymerization or cross-linking co-polymerization of the side groups.

16. The biopolymer matrix of claim 15 further comprising one or a mixture of two or more of the following compounds:

a polysulfated oligo- or polysaccharide or fragments thereof;

biocompatible polyanion which has the capacity to bind heparin-binding growth factors;

a proteoglycan containing glycosaminoglycan chains capable of binding to heparin-binding growth factors;

a functional analogue of heparin which binds or stabilizes heparin-binding growth factors;

monoclonal or polyclonal antibody or a microprotein wherein said antibody or microprotein has a high and selective affinity for molecular factors that can modulate the wound healing process, and wherein said microprotein can be obtained by phage display;

a therapeutically effective amount of a drug; and compounds having substantial affinity for the incorporated drug, so as to slow down the release of the drug from the matrix and/or stabilizing the drug.

17. A process comprising:

(a) providing a solution comprising:

(i) a methacrylamide modified gelatin and a polysaccharide, wherein the gelatin is modified with methacrylamide side groups which are capable of being radically cross-linked; or (ii) providing a solution comprising a gelatin and a vinyl-substituted polysaccharide, wherein the polysaccharide is modified with vinyl side groups which are capable of being radically cross-linked; or, (iii) providing a solution comprising a methacrylamide modified gelatin and a vinyl-substituted polysaccharide wherein the gelatin has been modified with methacrylamide side groups which are capable of being radically cross-linked and the polysaccharide has been modified with vinyl side groups which are capable of being radically cross-linked;

(b) radically inducing cross-linking polymerization or cross-linking co-polymerization of the side groups.

18. The composition of claim 2 wherein the drug is an antiseptic or a wound healing drug.

19. The composition of claim 18 wherein the drug is selected from the group consisting of an EGF, a FGF, a TGF-β, an IGF, a PDGF, and keratinocyte cell lysate.

20. The composition of claim 16 wherein the drug is an antiseptic or a wound healing drug comprising mitogens and/or their antagonists.

21. The composition of claim 20 wherein the drug is selected from the group consisting of an EGF, a FGF, a TGF-β, an IGF, a PDGF, and keratinocyte cell lysate.

* * * * *